(12) United States Patent
Slowey et al.

(10) Patent No.: US 7,927,548 B2
(45) Date of Patent: Apr. 19, 2011

(54) SPECIMEN SAMPLE COLLECTION DEVICE AND TEST SYSTEM

(75) Inventors: Paul D. Slowey, Vancouver, WA (US); Richard Herrig, Phoenix, AZ (US); James Wickstead, Mendham, NJ (US); John Ennis, Vancouver, WA (US); Paul Smith, Washougal, WA (US); Jason Giddings, Forest Grove, OR (US); Keith Seritella, Washington, NJ (US)

(73) Assignee: Bamburgh Marsh LLC, Vancouver, WA (US)

( * ) Notice: Subject to any disclaimer, the term of this patent is extended or adjusted under 35 U.S.C. 154(b) by 676 days.

(21) Appl. No.: 11/827,898

(22) Filed: Jul. 14, 2007

(65) Prior Publication Data

US 2008/0118397 A1 May 22, 2008

Related U.S. Application Data

(63) Continuation-in-part of application No. 11/045,180, filed on Jan. 27, 2005, now Pat. No. 7,618,591.

(51) Int. Cl.
*B01L 3/00* (2006.01)
*B01L 3/02* (2006.01)
*B01L 99/00* (2010.01)
*A61B 5/00* (2006.01)
*C12M 1/34* (2006.01)

(52) U.S. Cl. ........ 422/102; 422/100; 422/101; 600/573; 435/287.7

(58) Field of Classification Search ................. 422/100, 422/101, 102; 600/573; 435/287.7
See application file for complete search history.

(56) References Cited

U.S. PATENT DOCUMENTS

| | | | | |
|---|---|---|---|---|
| 4,859,610 A | * | 8/1989 | Maggio | 436/518 |
| 4,931,051 A | * | 6/1990 | Castello | 604/361 |
| 5,016,982 A | * | 5/1991 | Fergason et al. | 349/33 |
| 5,339,829 A | * | 8/1994 | Thieme et al. | 600/573 |
| 5,376,337 A | * | 12/1994 | Seymour | 422/101 |
| 5,393,496 A | * | 2/1995 | Seymour | 422/101 |
| D369,664 S | * | 5/1996 | Dye | D24/129 |
| 5,900,379 A | * | 5/1999 | Noda et al. | 436/518 |
| 6,248,598 B1 | * | 6/2001 | Bogema | 436/518 |
| 6,365,417 B1 | * | 4/2002 | Fleming et al. | 436/514 |
| 6,372,516 B1 | * | 4/2002 | Sun | 436/518 |
| 6,451,619 B1 | * | 9/2002 | Catt et al. | 436/514 |
| 7,225,689 B2 | * | 6/2007 | Wickstead et al. | 73/863.23 |
| 7,618,591 B2 | * | 11/2009 | Slowey et al. | 422/102 |
| 2002/0001539 A1 | * | 1/2002 | DiCesare et al. | 422/52 |
| 2003/0113906 A1 | * | 6/2003 | Sangha et al. | 435/287.2 |
| 2006/0057027 A1 | * | 3/2006 | Hudak et al. | 422/99 |
| 2007/0166198 A1 | * | 7/2007 | Sangha et al. | 422/99 |
| 2009/0306543 A1 | * | 12/2009 | Slowey et al. | 600/576 |

* cited by examiner

*Primary Examiner* — Lore Jarrett
(74) *Attorney, Agent, or Firm* — Rylander & Associates PC; Mark E. Beatty; Kurt M. Rylander

(57) ABSTRACT

A specimen sample collection device includes a handle having a sufficiency indicator and an absorbent pad partially contained within said handle. A specimen sample collection device and test system includes a handle having a sufficiency indicator, an absorbent pad partially contained within said handle, a pad compression tube insertable over said absorbent pad within said handle and around an end of said handle, and a collection tube having one or more sample chambers, attachable to said pad compression tube, and wherein said compression tube defines one or more chambers, and wherein when said collection tube is attached to said pad compression tube, the chambers are in fluid communication with said pad compression tube. A specimen sample collection device including a sufficiency indicator made up of a light pipe indicator window. A specimen sample collection device including an absorbent pad split and divided into two lengths connected at a base. A specimen sample collection device including a bar code identification. A specimen sample collection device and test system including a lock and key securing mechanism. A specimen sample collection device including a handle one or more analyte test strips A specimen sample collection device and test system including a reader.

18 Claims, 13 Drawing Sheets

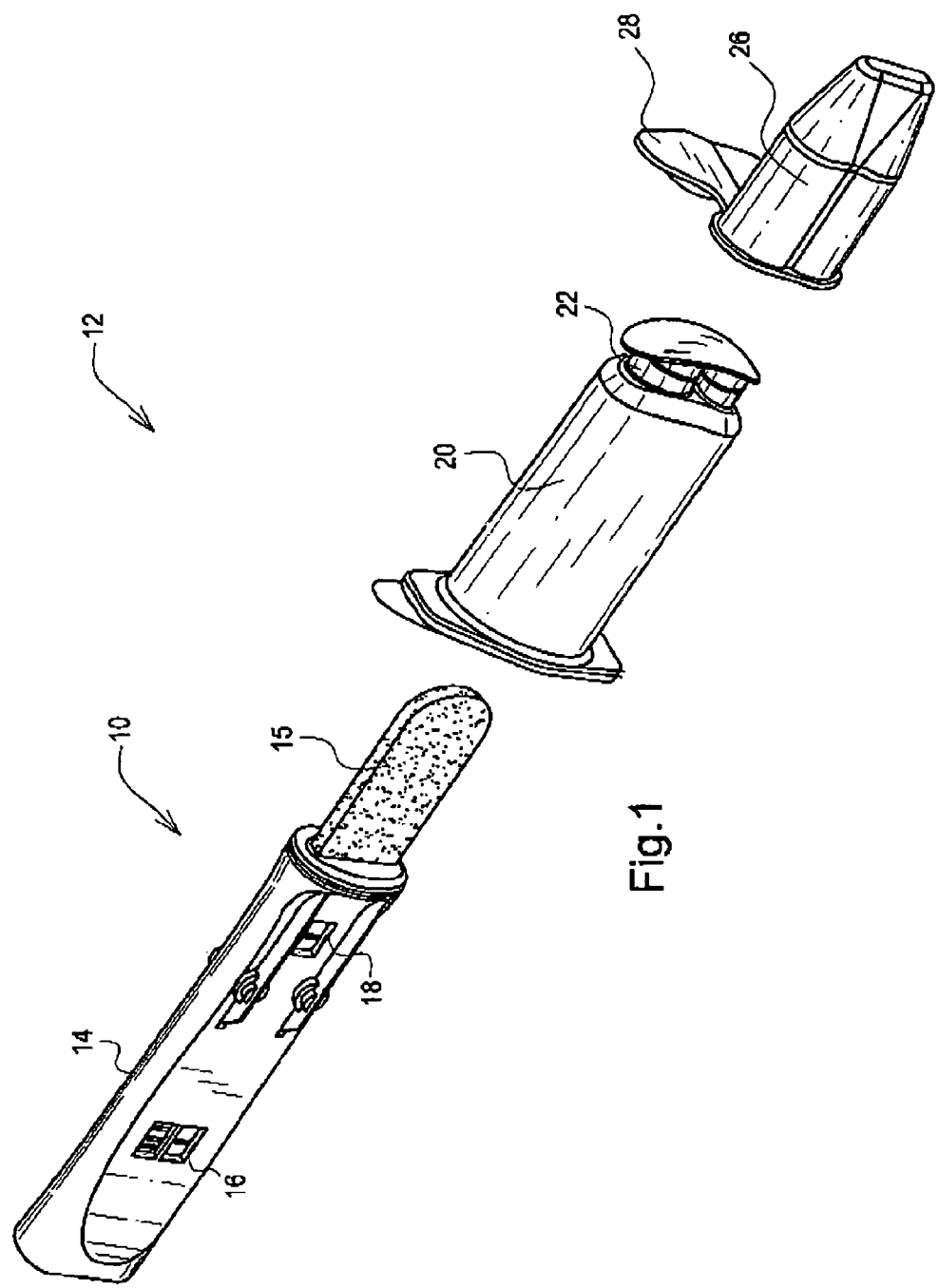

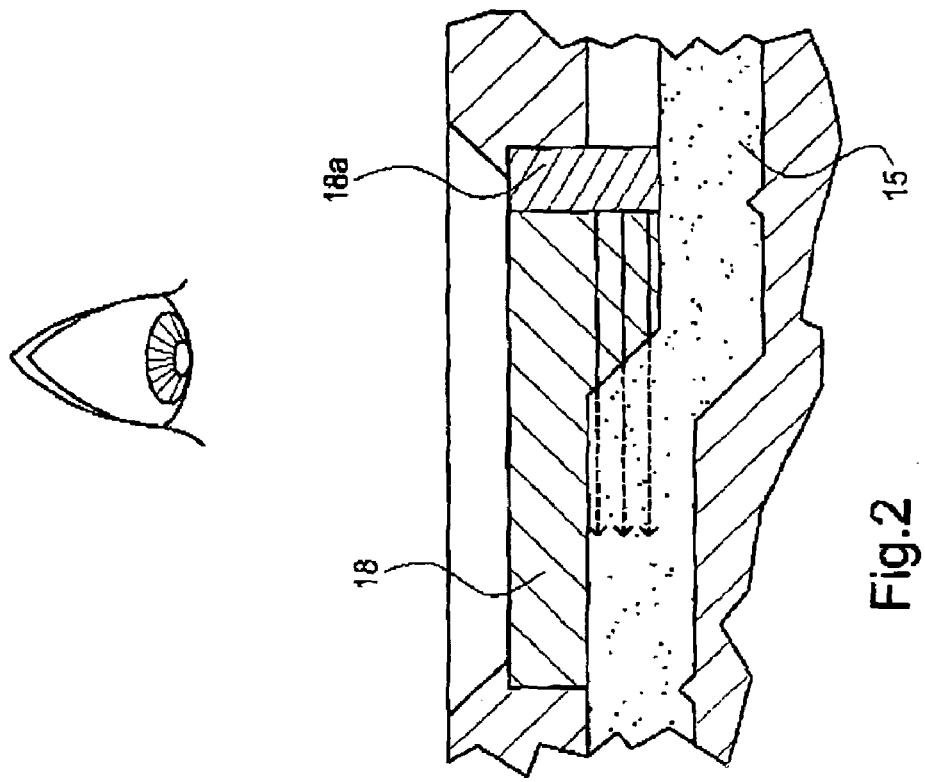
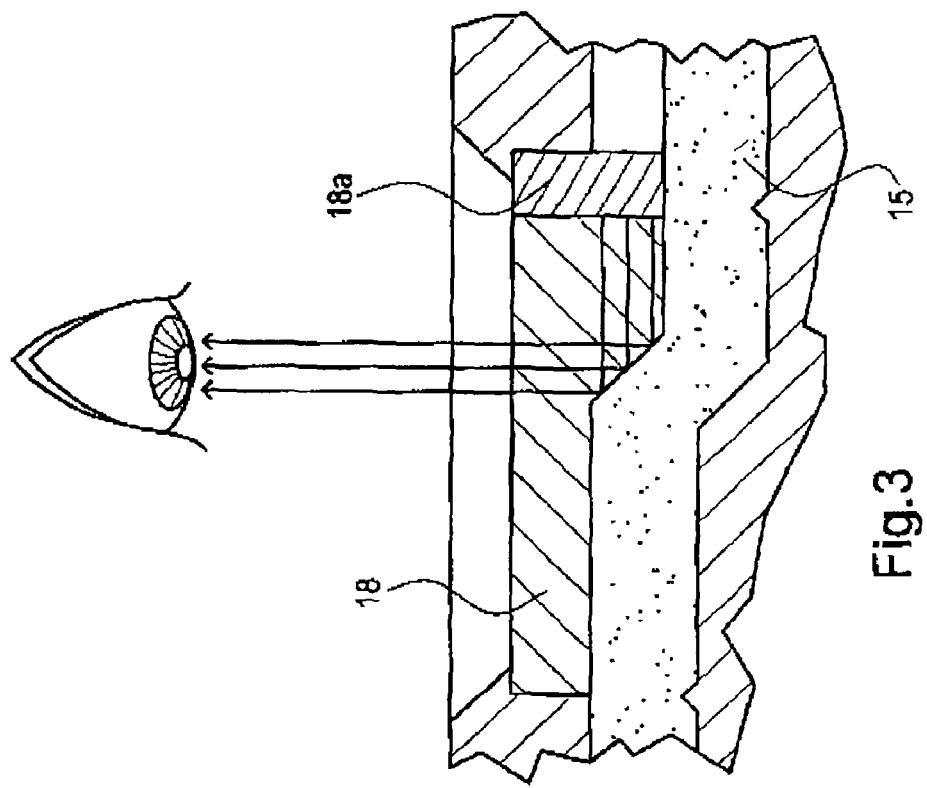

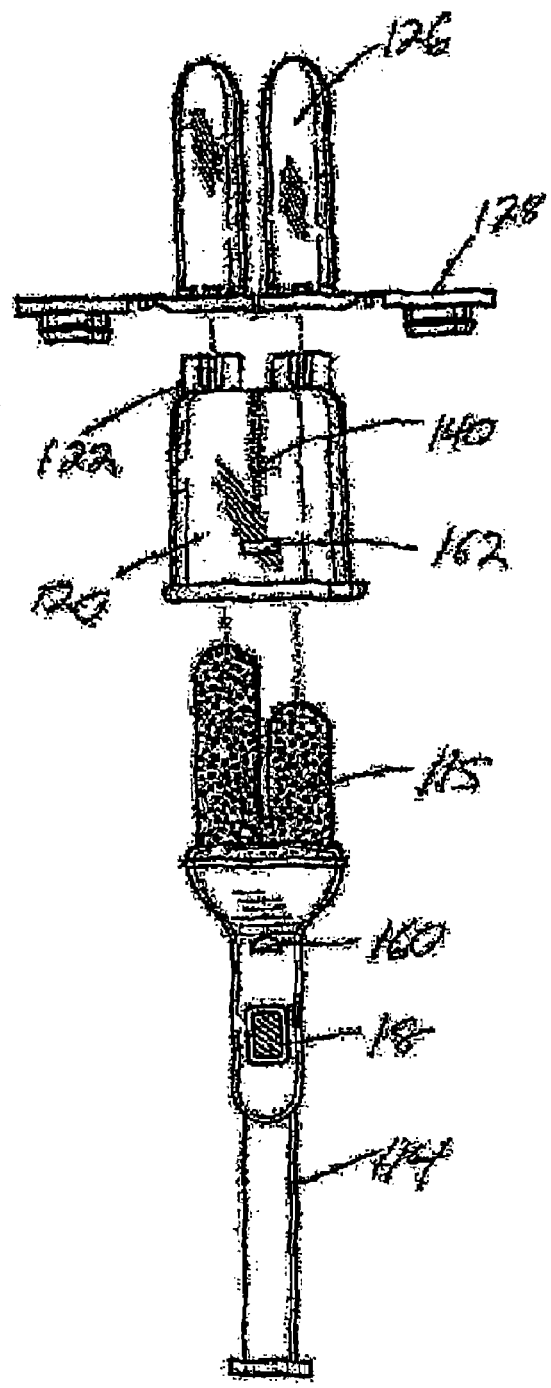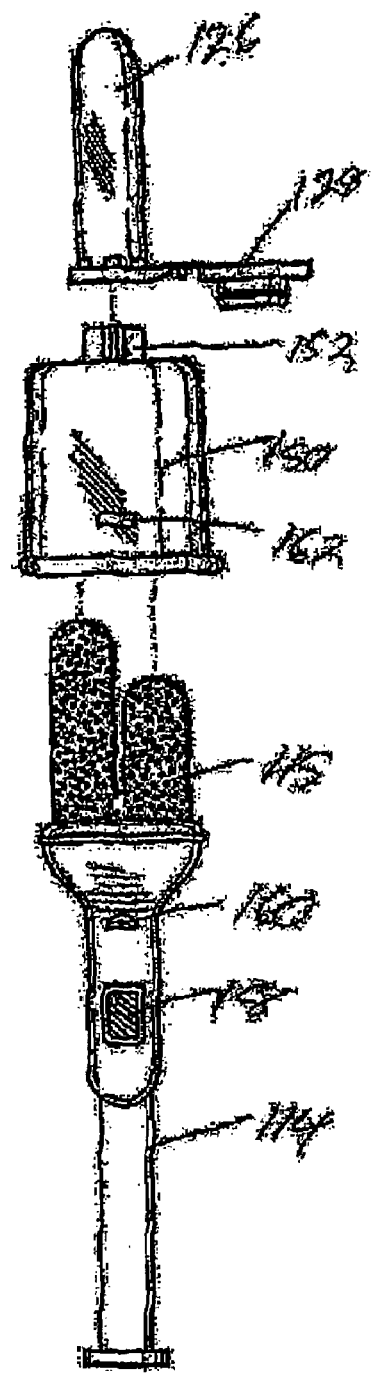
FIG. 8
FIG. 9

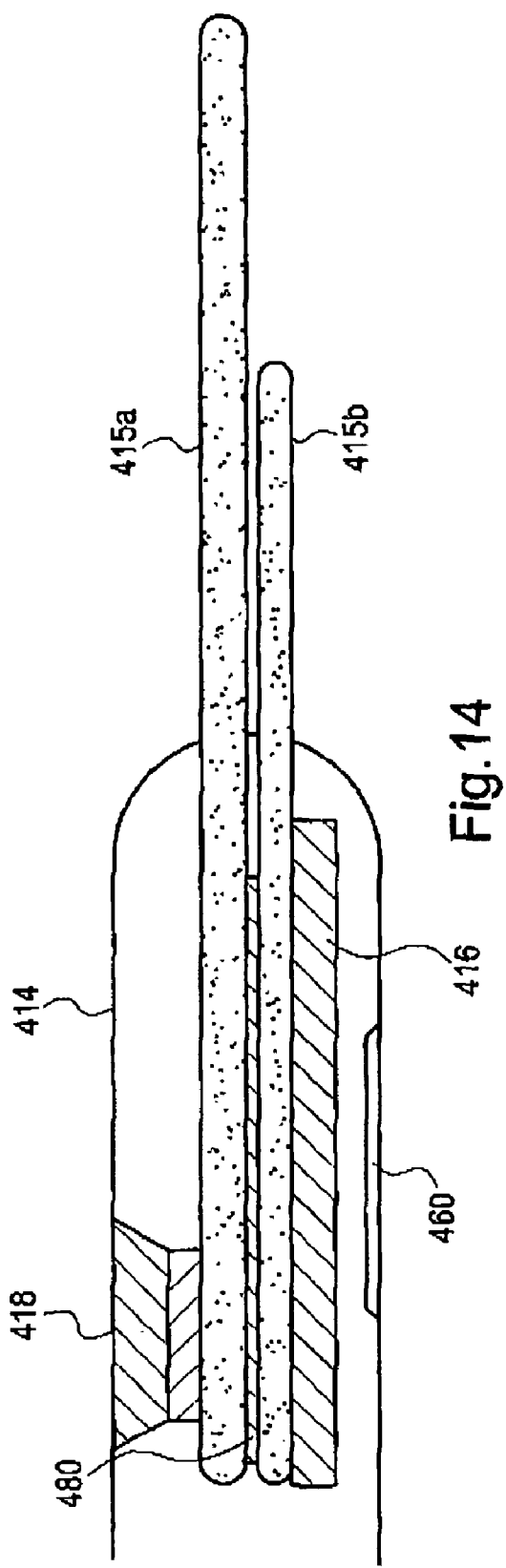

SPECIMEN SAMPLE COLLECTION DEVICE AND TEST SYSTEM

CROSS-REFERENCE TO RELATED APPLICATION

The present application is a continuation-in-part of and claims priority to prior U.S. patent application Ser. No. 11/045,180 filed on Jan. 27, 2005 now U.S. Pat. No. 7,618,591.

FIELD OF THE INVENTION

The present invention relates to devices and methods for the collection of fluids, and more particularly to devices and methods for the collection of fluids and methods for testing samples so obtained for fluids including bodily fluids such as saliva.

BACKGROUND

Traditional methods of testing for diseases, drugs and other antigens in humans have up until the last few years been predominantly done using blood samples. These samples collected in laboratories at the request of physicians require that blood drawn by a trained phlebotomist is sent to a laboratory and the serum component comprising a predominance of immunoglobulins, containing antibodies to the disease or disease state in question, is tested using a variety of available test kits to assist in the diagnosis of various diseases including infectious diseases, cardiovascular diseases, cancers and many others. Such samples can also be tested for the presence of non-disease analytes such as metals, minerals, DNA, bacteria and organic molecules among others.

Under current standardized laboratory practices, it is necessary to confirm any initially positive result obtained from diagnostic or analytical testing with a more sensitive (accurate) method. This, in fact is true for most, if not all diagnostic tests used today, including, as an example, HIV tests, which are confirmed by more definitive methods such as Western blot techniques or immunofluorescence (IFA) assays. In the case of drug tests, for instance, performed in criminal justice settings (at the police car, in correctional facilities, in drug courts, etc.) or at the workplace, by way of two examples, confirmation is carried out using gas chromatography-mass spectrometry (GC-MS), gas chromatography-mass spectrometry-mass-spectrometry (GC-MS-MS) or liquid chromatography-mass spectrometry-mass spectrometry (LC-MS-MS) on a second sample taken from the subject. Other diagnostic and screening methods require similarly accurate methods for confirmatory purposes.

The United States Substance Abuse Mental Health Services Administration (SAMHSA), the designated body responsible for regulating Federal drug testing in the United States, has recently prepared guidelines for the introduction of new tests and sample collection procedures for drug tests using so-called, "alternate" specimens. These sample types include saliva (or oral fluids), hair and sweat. These guidelines define the need for (1) a confirmatory specimen to be collected at the time of the initial sampling, (2) defined specimen volumes to be collected and (3) expected drug cut-off values, among other requirements.

The need for duplicate, or a multiplicity of mutually distinct samples taken from the same source at the same time is part of a general trend being observed in many areas of the diagnostic and analytical testing businesses. The main reason for this increasingly important trend is the legal implication of being able to definitively rule out any potential contamination of the test sample during the testing process. The obvious consequences of an incorrect diagnosis of HIV for a patient or erroneous DNA results in the case of a criminal case are just two examples of where 100% certainty of sample integrity are paramount and are contributing reasons for the development of this particular invention. This potential legal implication has had an impact on general testing protocols and as a result healthcare and other professionals are now more cognizant than ever of the need to collect a "pure" sample or samples then ensure that those samples are analyzed to produce accurate results. During the testing process absolute "chain-of-custody" rules are enforced to ensure that no adulteration or contamination of the specimen occurs. This is not always possible in current testing protocols as there are opportunities for sample contamination or sample tampering. This is true for any test whether done on blood, serum, saliva, nasal secretions, vaginal discharge or any other sample where information obtained relates to a diagnosis of disease or disease state. Such information is taken in conjunction with any additional information available to the person making a decision relating to interpretation of the results obtained.

Despite the fact that saliva has been used as a diagnostic fluid since Ancient Chinese times, when the "Rice Test" (which relied on the inhibition of saliva as a determinate of guilt) was used, it is only over the last few years that salivary testing has taken on much greater significance. There are several important factors, which have contributed to this change: (1) The increase in popularity of non- or less-invasive testing methods; (2) the availability of more sensitive antibodies and antigens for detection of immunoglobulins in saliva; (3) new technologies in the area of point-of-care testing; (4) a need for more rapid results; (5) acquisition of serum/blood involves patient discomfort and can cause difficulty particularly where young children or intravenous drug users are concerned; (6) use of venous blood to collect serum requires capital equipment and involves an initial processing step, which adds significant time to result turnaround and has additional cost implications and also; (7) a general movement away from centralized laboratory testing towards "near-patient" testing, also called "point-of-care" testing.

The National Institutes of Health (NIH) recognized the value of salivary testing as early as 1993 and recent symposia orchestrated by this organization, for instance a meeting held in 1999, organized by NIH's National Institute of Dental and Craniofacial Research (NIDCR) division has helped increase the profile of testing using oral fluids. NIH, through various divisions, has since been encouraging companies with expertise in this area to apply for funding for new projects aimed at introducing novel tests using non-invasive samples for laboratory and point-of-care applications.

The insurance testing industry uses saliva as a sample matrix for applicants wishing to purchase specific life insurance policies as a safeguard measure prior to writing policies. In these situations applicants are tested for HIV, cotinine (nicotine) and cocaine using a testing device called "OraSure" from OraSure Technologies, which collects oral fluids for subsequent testing under laboratory conditions. Each of the major insurance testing laboratories in the United States performs a significant number of oral fluid tests on an annual basis.

In April 2004 OraSure Technologies was successful in gaining FDA approval for its OraQuick® HIV ½ rapid test for oral fluid diagnosis of the HIV viruses type 1 and type 2. Previously the test had been approved by the agency for whole blood, serum and plasma only.

In a separate area drugs of abuse are routinely detected from oral fluids collected in the workplace, in criminal justice settings and in hospitals using OraSure Technologies' "Intercept™" device and associated range of ELISA microplate assays. In this case a panel of 5 "abused" drugs or more are measured under laboratory conditions.

Rapid testing devices using saliva have recently appeared, which may be used at the "point-of-care". These devices can collect and perform immediate testing for several drugs of abuse but these suffer from poor performance for certain tests at the present time, particularly Tetrahydrocannabinol (THC) or its major metabolite 11-nor-Δ9-Tetrahydrocannabinol. Examples of this type of device are the OraTect™ test from Branan Medical Corporation, the OraLine assay from Sun Biomedical and the Cozart BioScience RapiScan device, among others.

Up until now urine based rapid drug testing has been performed preferentially due to availability, cost, and to a certain extent, a lack of salivary tools incorporating some of the features described in this invention. While rapid urine kits are widespread they suffer from issues related to "chain-of-custody", the need for facilities to collect urine specimens discreetly under appropriate supervision and are easily adulterated by knowledgeable users, who can "cheat" such tests.

Electronic reading, hand-held devices, such as the Cozart BioSciences RapiScan instrument are also now available outside of the United States, that allow immediate drug testing to be done from oral fluids at the roadside and other field settings. This technology requires sample collection from the donor then immediate testing on site. This concept may well be duplicated in the future, as technologies to "miniaturize" testing platforms, improves.

The FDA has approved a laboratory HIV test, OraSure HIV-1 for testing for the HIV-1 virus from oral fluid as well as a Western blot confirmatory test, which also uses oral fluids. Both have been used in a Public Health setting in the United States for over five (5) years.

In addition the FDA has also approved saliva tests for pre-term labor (SalEst™, salivary estriol, from Biex, Inc), a salivary alcohol test (QED®, OraSure Technologies), a cortisol assay (Salimetrics, Inc.) as well as a panel of saliva-based drug assays (Intercept, OraSure Technologies) through the 510(k) clearance system. A number of other oral fluid drug testing products are undergoing regulatory approval, so in the next 12-24 months we might expect to see several other products available in the U.S. Furthermore, "investigational use" tests are available for immunoglobulins, for example sigA (for use in psychological disorders, stress and athletic performance), therapeutic drugs (for instance lithium, theophylline, AZT), tumor markers (e.g. Her-2/neu), bacterial antibodies such as *helicobacter pylori* and even genomic detection of mitochondrial DNA (for criminal justice applications) using oral fluids as the preferred specimen matrix.

Emerging methodologies based on microfluidic technology requiring only small quantities of specimen samples are approaching the market. These devices work on virtually any specimen matrix including, but not limited to, saliva, urine, whole blood, serum, and other fluids. Such techniques have already found use in the arena of biodefense monitoring, high throughput screening methods, high performance liquid chromatography (HPLC) and other analytical techniques. These devices, which are being developed in one particular area for use by special intelligence forces, who are required to test for chemical and biological agents in soil, water and other samples before troops arrive at a battle site or during peacekeeping to monitor biological or environmental samples, may be seen as another area where this invention will find application.

These are a few of the many instances where saliva is viewed as a viable sample matrix for testing purposes. A number of devices in use today have provided means for the collection of bodily fluids including saliva and urine among others. One FDA-cleared fluid collection device used predominantly for saliva collection and testing has been shown to be potentially unsafe in pediatric patients. The Saliva•Sampler™ device from SDS, Inc. utilizes perforations present on filter paper to facilitate removal of the filter paper for subsequent saliva separation and testing. The device is placed under the tongue to accumulate sublingual whole saliva, collected by leaving the sampling device, consisting of a filter paper material attached to a plastic stem, in position until a sample indicator built into the device changes color confirming sample sufficiency. The process requires that the subject not chew, bite or unnecessarily move the device during the collection procedure. In pediatric patients, particularly, this can be a problem as children have a tendency to chew on materials placed in the oral cavity. In infants, separation of the filter paper prematurely can result in choking.

In another previously described example, an alternate FDA-approved oral fluidcollection system from OraSure Technologies, Inc., known as OraSure®, incorporates salts impregnated on to the collection medium in the form of a "hypertonic" solution. According to the manufacturers, the purpose of the salts is to facilitate ready absorption of oral fluids (oral mucosal transudate) from the gingival crevices and thereby reduce sampling time. In practice when the OraSure® device is placed in the oral cavity, the taste of the salts on the device medium may be distasteful to potential users.

These and other currently available devices fail to address a growing need for efficient collection of bodily fluids including saliva for applications including analytical or diagnostic testing under laboratory, field or point-of-care testing conditions, for instance, whereby a pure sample of fluid, for example saliva, is collected from a subject and split into multiple chambers, thereby providing a means for initial specimen testing analysis or storage, for confirmation or supplementary testing and simultaneously providing a mechanism for confirming sample sufficiency prior to any subsequent testing or analysis of the constituents of the bodily fluid so collected.

Lateral flow immunochromatography (ICT) tests have been around for over a decade and are a direct descendent of thin-layer chromatography (TLC) techniques pioneered during the 1970s. The technology offers some benefits including cost efficiencies, user-friendliness and the availability of immediate test results. Over the last decade in particular, the availability of high quality raw material components, the growing movement towards near patient or point-of-care ("POC") testing, coupled with a need for rapid results, has led to an "explosion" in the development and commercialization of both flow-through and lateral flow devices based on immunochromatographic test principles. These devices form part of a rapidly growing industry for diagnostic tests performed outside of the laboratory.

A variety of ICT tests are now available including as examples OraSure Technologies' rapid oral fluid test, OraQuick HIV ½, Quidel Corporation's Quick-Vue *Streptococcus* A and *Helicobacter pylori* rapid tests, Meridian Biosciences' ImmunoCard assays for Respiratory Syncticial Virus (RSV) and *Clostridium Difficile* (*C. Difficile*) and Roche Diagnostics' TestCup drugs of abuse tests among a multitude of others.

Technologies other than ICT are equally adaptable to rapid testing. These include latex agglutination, dot-blot tests, microarrays and others.

Of the above rapid test examples and those currently in existence, only OraSure Technologies has been successful in commercializing a rapid, oral fluid test, OraQuick HIV ½, despite the fact that oral fluid, point-of-care tests represent an attractive alternative to current testing methodologies. This may be due, in part, to current data requirements for approval of rapid tests in the U.S. This is expected to change as a result of OraSure's success with OraQuick® HIV ½ and the emergence of saliva-based drug testing assays.

In order to meet the needs of a growing Public Health demand in the U.S. it is important for would-be manufacturers to integrate test strip technologies similar to those mentioned above with a simple-to-use, integrated platform system that can deliver rapid test results, safely and cost-effectively, for a range of diseases or analytes in a non-invasive manner. This is especially important in view of Centers for Disease Control (CDC) estimates that suggest that, of 2.1 million people tested at Publicly-funded Government testing sites using traditional (laboratory) testing methods in the US for the HIV virus, approximately 33% do not return to receive their results and may unwittingly go on to infect others if they are in fact HIV-positive. As the key to all disease prevention is early detection, accurate and early detection using rapid tests can have a major impact on reducing disease incidence.

In needle-averse populations, for instance, small children, pregnant women and hemophiliacs, the opportunity to provide oral fluid or saliva collection and immediate testing as an alternative to blood-based systems would be welcomed. Similarly general practitioners and health professionals would see an opportunity to provide testing opportunities in non-traditional testing sites, such as in the privacy of the patient's home, in nursing homes, remote clinic settings and even over the counter in a pharmacy environment.

Cozart BioSciences (UK, www.Cozart.co.uk)) has described the use of a hand-held device known as RapiScan, which tests for several illicit drug entities from oral fluids. This reading system is not fully integrated and requires a separate collection step prior to testing the specimen. OraSure Technologies (www.OraSure.com) has also described in a recent US patent application (Application Number unknown at this time), the use of a sample collector and test device. In this example also, sample collection is distinct from the specimen testing process.

SAMHSA has proposed in its 2004 guidelines for alternate specimen testing that minimum oral fluid collection volumes are to be 2 mL of clean specimen.

None of the available prior art provides for expressing an oral fluid sample from a subject directly onto a diagnostic test strip, providing a mechanism for determining sample volume adequacy and visually reading qualitative and/or quantitative results from the test strip through a small window in an integrated one-step manner.

The following represents a list of known related art U.S. Pat. No. 5,283,038 issued Feb. 1, 1994, U.S. Pat. No. 5,260,031 issued Nov. 9, 1993, U.S. Pat. No. 5,268,148 issued Dec. 7, 1993, U.S. Pat. No. 5,393,496 issued Feb. 23, 1995, U.S. Pat. No. 5,380,492 issued Jan. 10, 1995, U.S. Pat. No. 5,376,337 issued Dec. 27, 1994, U.S. Pat. No. 6,267,722, U.S. Pat. No. 6,027,943, U.S. Pat. No. 6,187,598, U.S. Pat. No. 5,965,453, U.S. Pat. No. 5,393,496, U.S. Pat. No. 4,943,522, U.S. Pat. No. 4,895,808, U.S. Pat. No. 6,372,516, U.S. Pat. No. 6,046,058, U.S. Pat. No. 5,962,336, U.S. Pat. No. 5,238,652, U.S. patent application Ser. No. 10/061,036 by Lloyd Simonson, U.S. patent application Ser. No. 10/060,605 by Lloyd Simonson, U.S. Pat. No. 6,627,152, U.S. Pat. No. 6,727,879, U.S. Pat. No. 5,922,614 to Edward Cesarczyk, U.S. Pat. No. 6,489,172. None of the above inventions and patents, taken either singularly or in combination, is seen to describe the instant invention as claimed.

SUMMARY AND ADVANTAGES

A specimen sample collection device and test system includes a handle having a sufficiency indicator and unidirectional locking teeth on opposing sides of the handle, an absorbent pad partially contained within said handle, a pad compression tube insertable over said absorbent pad within said handle and around an end of said handle, wherein the pad compression tube includes locking holes on opposing sides distributed along its length to engage the unidirectional locking teeth, and a collection tube having one or more sample chambers, attachable to said pad compression tube, and wherein said compression tube defines one or more chambers, and wherein when said collection tube is attached to said pad compression tube, the chambers are in fluid communication with said pad compression tube. A specimen sample collection device includes a sufficiency indicator made up of a light pipe indicator window. A specimen sample collection device includes a sufficiency indicator made up of a light pipe indicator window with a spring compressor. A specimen sample collection device includes an absorbent pad split and divided into two lengths connected at a base. A specimen sample collection device includes a bar code identification. A specimen sample collection device and test system includes a lock and key securing mechanism. A specimen sample collection device includes a handle containing one or more analyte test strips A specimen sample collection device and test system includes an electro-optical a reader. A specimen sample collection device and test system includes a first absorbent pad in fluid communication with a sample adequacy indicator, which is in parallel with a second absorbent pad in fluid communication with a lateral flow analyte test strip. A specimen sample collection device and test system includes a first absorbent pad in fluid communication with a sample adequacy indicator, which is in parallel with a second absorbent pad in fluid communication with a lateral flow analyte test strip, with an impermeable membrane separating the first and second absorbent pads.

The specimen sample collection device and test system of the present invention presents numerous advantages, including: (1) ability to collect appropriate volumes of specimen sample and confirmation sample using a split (fork-shaped) collection medium; (2) ergonomically correct design; (3) simple to use; (4) ability to adapt to new testing requirements; (5) sample containment with minimized chance of contamination; (6) utilizes an absorbent pad collection medium rather than a filter paper collection medium; (7) provides a unique sample indicator design that does not utilize a compressible sponge or polymeric bead; (8) provides a unique sample indicator design that does not involve disposing an indicator on filter paper; (9) provides a unique sample indicator design that does not require an adequacy indicator separate from the collection medium; (10) utilizes a collection medium that does not require a rectangular or paddle shape; (11) allows for samples to be removed from individual compartments or chambers and channeled directly or pipetted if necessary, directly into an alternate receptacle for further analysis or testing; (12) allows for removal of the specimen directly using high-throughput automated equipment, which can speed up sampling and analysis tremendously. (13) allows for collection of mutually distinct samples for initial testing or analysis and follow up or supplementary testing either immediately or at a later date; (14) allows for use of "tailored" buffer solutions designed to protect the integrity of various different analytes or samples collected; (15) utilizes multiple absorbent materials to maximize the retention and release properties of the invention; (16) allows for testing samples collected immediately using available lateral flow immunochromatographic test strips to deliver test results at the point of care; (17) allows for collection of specimen without the need for an additional filtration or centrifugation step; (18) requires no expensive capital equipment to collect and process the sample; (19) allows for individual sample identification; (20) allows for a variety of sample collection tubes to be attached to the end of the invention depending upon sample volume requirements and whether single or dual sampling is required; (21) requires minimum manipulation of fluid specimen; (22) minimizes the chance for contamination of the sample collected; (23) minimizes the chance of tampering with the sample collected; (24) provides the ability to rule out contamination; (25) reduces the opportunity for misdiagnosis; (26) provides the ability to work within "chain-of-custody" protocols; (27) provides the ability to obtain a rapid test result and a confirmatory result; (28) utilizes an intact pad material and does not require that the absorbent pad material be separated from the main sampling device, so there is a significantly reduced chance of the pad separating in the subject's mouth when used in normal practice; (29) does not require the use of any salts or hypotonic solutions impregnated in the collection medium to improve collection time; (30) provides the ability to deliver fluids to two test strips or two separate receiving ports at the same time; (31) parallel absorbent pads allow a more compact design; and, (32) parallel absorbent pads allow using pads with different absorbent characteristics to optimize results.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

FIG. 1 shows an embodiment of a specimen sample collection device and test system.

FIG. 2 shows a light pipe indicator window over a dry absorbent pad.

FIG. 3 shows a light pipe indicator window over a saturated absorbent pad

FIG. 5c shows the view of FIG. 5a from the side.

FIG. 6b shows the view of FIG. 6a from the side.

FIG. 8 shows another embodiment of a specimen sample collection device and test system.

FIG. 9 shows another embodiment of a specimen sample collection device and test system.

FIG. 14 shows a cross-sectional view of an embodiment of a specimen sample collection device with parallel absorbent pads.

DETAILED DESCRIPTION

Figure 1A:
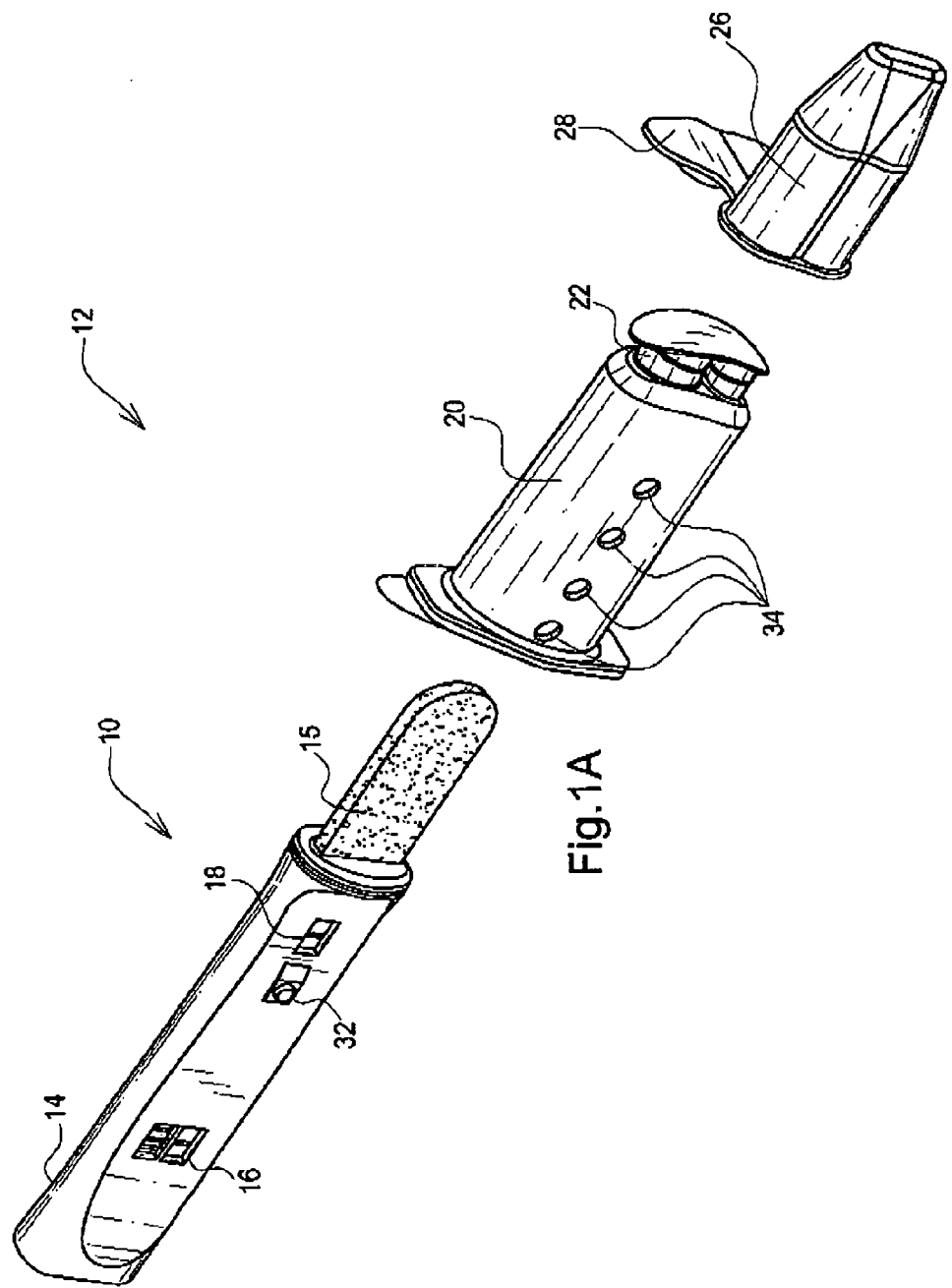
FIG. 1a shows a schematic view of a specimen sample collection device and test system with a pad compression tube attached to a handle including locking teeth.

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

As shown in FIGS. 1-4, a specimen sample collection device 10 includes a handle 14 with a sufficiency indicator, such as a light pipe indicator window 18, and an absorbent pad, which can be a rounded tongue absorbent pad 15. As shown in FIG. 1, a specimen sample collection device and test system 12 includes a specimen sample collection device 10, a pad compression tube, which can be a dual outlet single channel compression tube 20, and a collection tube, which can be a chambered collection tube 26

Absorbent pad 15 fits partially within the handle. As shown in FIGS. 1, 4, 7, and 10 at 15, absorbent pad can be rounded to provide the advantage of comfort to the sample subject. As show in FIGS. 8 and 9 at 115, the absorbent pad can be split, i.e., divided into two parts and connected at the base of the pad to allow for dual sample collection. The split absorbent pad 115 can be prong- or fork-shaped or have splits of varying length. Those of skill in the art are aware that the absorbent pad can be divided into more than two parts. In this embodiment the split absorbent pad 115 is configured such that one prong of the pad can absorb at least 1.0 mL of specimen, and the other pad can absorb at least 0.5 mL of specimen, when a highly absorbent pad material e.g. Ahlstrom 320 or Schleicher & Schuell 300 grades are chosen. When a split, divided, prong or fork shaped absorbent pad is placed into the test subject's mouth each split or division of said absorbent pad absorbs saliva at the same time, thus collecting identical saliva samples. One of skill in the art would also realize that the absorbent pad could be two or more separate and distinct absorbent pads. Absorbent pad can also be provided with a bifurcated-end in a smooth "m" shape on the end of the pad interior of the handle to deliver saliva to the ends of two test strips simultaneously.

The absorbent pad soaks up specimen when placed in a specimen atmosphere, such as for example, soaking up saliva when placed in a subject's mouth, preferably under the tongue. Absorbent pad is not filter paper. Filter paper is designed specifically to have porous openings to have control or "filter" the size of material passing through it. The purpose of the absorbent pad is to collect and disperse a high volume of liquid sample yet remain relatively rigid through the sample collection procedure. Thus, an advantage is obtained by using an absorbent pad rather than filter paper. Absorbent pad may be a variety of different materials that will absorb liquid and release or transmit said liquid following an action carried out to facilitate removal of said liquid from the pad.

Pad materials have a variety of properties, which may affect the ability of a substance to adhere (or bind) to that specific absorbent pad material effectively, and also for that material to be suitably released from the pad when required. One particular property is a material's hydrophobic or hydrophilic characteristics. Hydrophilic materials are readily "wet" with aqueous solutions and so aqueous based fluids, such as saliva, urine, whole blood, vaginal fluid, etc. (containing antibodies, minerals, and other analytes of interest) will be readily absorbed by hydrophilic pad materials and released effectively. In the preferred embodiment of this invention for example, absorbent pad material is made up of hydrophilic materials from a list including Ahlstrom materials catalog numbers 270 and 320, Schleicher & Schuell catalog numbers 300 and 900 among others. Experimentation has shown that a large cross-section of substances to be detected or measured in fluids can be carried out using one of these versatile products. Hydrophobic pad materials will not adequately "wet" in aqueous solutions but will be wetted in low surface tension liquids such as alcohols, hence the need for the addition of low alcohol concentrations in any buffering system used.

Those skilled in the art know that numerous materials meeting these requirements exist, such as various cotton linters, for example Schleicher & Schuell (US) papers 300, 900, 903 or 2992, fiber composite materials such as materials available from Ahlstrom (US) for instance Ahlstrom 270, a multi-purpose cellulose material that has been used for fluid collection and release and Ahlstrom grade 320 material, a material with hydrophobic characteristics. Also glass fiber, certain polymeric materials, spunbound polyester materials (e.g. Hollytex brand from Ahlstrom, (US), extruded fibers, other cellulose papers manufactured from raw material cellulose (e.g. Ahlstrom Paper group (US) and Filtrona (US) Transorb®) materials), mixed fiber papers (e.g. Whatman (UK) Pads S9036-2009) as well as two-ply materials for example. The properties of these materials vary from absorbent materials with low protein binding capability to those with high binding capacity. Materials are available in various thicknesses and sizes and may be easily customized to suit the specific intended application for the pad material. Already, a diverse range of product materials is available form several sources including Schleicher & Schuell, Ahlstrom, Filtrona, Porex, Whatman and others as described above. These materials are typically manufactured under strictly controlled conditions to ensure uniform composition and absorption/release of fluids from the pad. Several of the afore-mentioned materials have been widely used as diagnostic and analytical testing components and have been certified as suitable for these purposes. Those skilled in the art know that absorbent pad materials may also include hydrophilic or hydrophobic components bound, or integrated into the material, such components being capable of modifying the absorption and release characteristics of the absorbent pad as well as the speed of uptake of the sample fluid under consideration. In the majority of cases antibodies minerals and substances will be readily removed from the absorbent pad upon squeezing the pad in the compression tube according to the operational instructions supplied herein. However, in certain instances, materials that are difficult to remove e.g. hydrophobic materials including progesterone, testosterone, estradiol, other steroid hormones and Δ9-Tetrahydrocannabinol (THC), will be collected in a further embodiment using a pad with hydrophobic properties. In this embodiment a small percentage of low molecular weight alcohol (ethanol, methanol or butanol, for instance) at a concentration of 0.1%-4.0% is added.

The binding characteristics of various protein and other molecules to the absorbent pad is another important factor. This particular property influences the nature of the binding of a given material to absorbent pad materials and is carefully considered when choosing products for a given application. Materials with high-binding characteristics may in some instances be used to encourage removal of certain analytes from the oral cavity, which may be difficult to obtain using pad materials with lower binding characteristics. In these cases, release agents such as alcohols, Tween 20 and others may be used.

Other properties, which can impact the performance of absorbent materials and hence the ability to collect an optimum fluid specimen include thermal stability, pore size and pad size. The dimensions and materials used in the preferred embodiments of this invention including Ahlstrom 270 & 320, Schleicher & Schuell 300 & 900 cellulose materials and others have been well characterized by the manufacturers and are also available in published works.

To one skilled in the art there are also a spread of materials, which offer a choice of "wicking rate", meaning the rate at which sample fluid is absorbed by the paper or pad material, so it is important for optimization purposes to work with individual manufacturers of such products to choose the optimum characteristics necessary to achieve the best results.

To one skilled in the art it is further apparent that modification of the properties of the absorbent pad can be made by the addition of various agents at the time of manufacturing the pad material. This invention has been conceived as a means of providing a method for customization and optimization of the properties of pad materials for a wide range of specific applications for which fluid collection is required. Further it is understood by one skilled in the art that modification of the dimensions of the pad (for instance thickness, width, height and others) can modify the absorption characteristics of the pad material. Materials such as those cited here are available through a number of companies including Whatman (UK), Ahlstrom (Finland), Schleicher and Schuell (US), Porex and Filtrona (US), which are chosen here by way of examples. While the above list of materials is considerable, these may or may not be suitable for the collection of certain types of specimens in fluids, for example steroid hormones, THC and certain other drug substances and others, for instance, which have a tendency to "stick to" certain pad materials and can be bound tightly. An embodiment of this invention therefore, teaches a method of using alternate pad materials in order to obtain the optimum system for collection and subsequent testing or analysis of certain hormones, drugs and any materials likely to cause difficulty in analyte removal from the pad. The ability to provide flexible options for pad materials is a novel invention. An advantage of this is that the pad material may be modified and optimized to suit the subsequent analysis, testing, or other action to be performed.

As shown in FIG. 1a, pad compression tube 20 may include locking holes 34 located on the opposing faces of handle 14 to engage locking teeth 32 which are located on the corresponding opposing faces of pad compression tube 20. Teeth 32 are preferably unidirectional to allow pad compression tube 20 to slide easily onto handle 14 but prevent removal. Locking teeth 32 are sloped away from outlet ports 22 to facilitate inserting into compression tube 20. Locking holes 34 are spaced along the length of pad compression tube 20 to allow pad compression tube 20 to lock in progressively tighter positions. In operation, locking holes 34 engage locking teeth 32 to ensure absorbent pad(s) 15 remain compressed to provide adequate liquid sample is separated for retention and testing, and prevents inadvertant reuse to inhibit spread of infectious diseases. Locking holes 34 also provide an air escape path to allow full compression of absorbent pad 15 without forcing liquid sample back into the cavity of handle 14.

Figure 11:
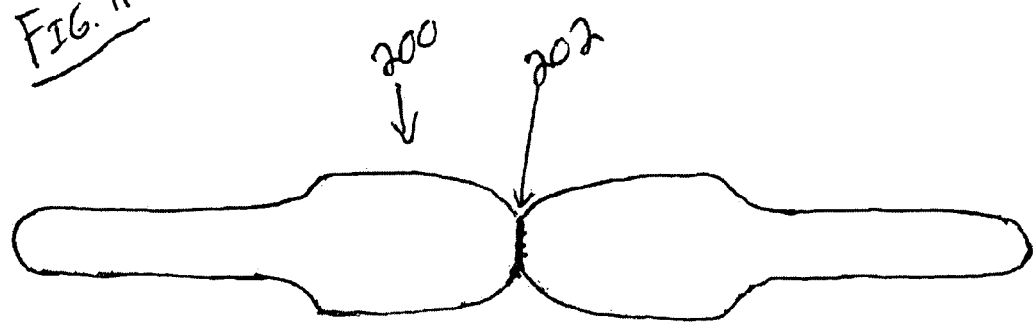
FIG. 11 shows an embodiment of an absorbent pad.
Figure 12:
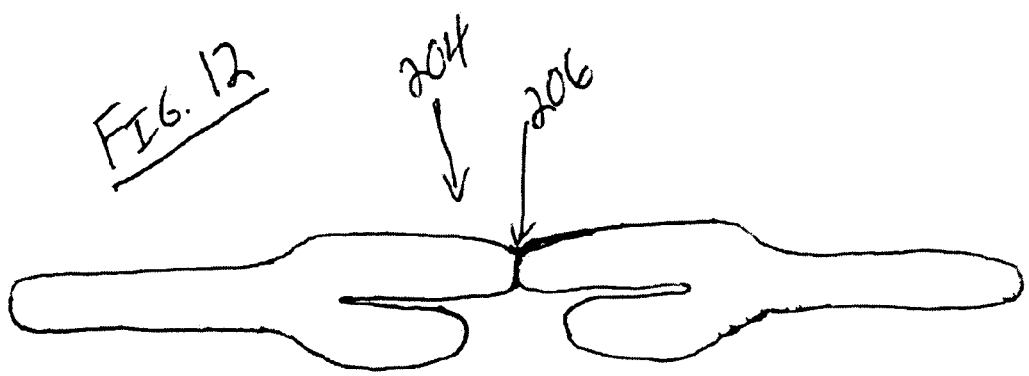
FIG. 12 shows another embodiment of an absorbent pad.

In an alternative embodiment, as shown in FIGS. 11, 12, absorbent pad can be a folded in half providing a double layer absorbent pad to provide additional structure for the absorbent pad and increase the surface area and absorption volume. FIG. 11 at 200 shows one possible shape, with the pad folded upon itself along the fold line at 202, which can be used with the specimen sample collective device 10. FIG. 12 at 204 shows a split absorbent pad shape, with the pad folded upon itself along the fold line at 206.

Figure 3A:
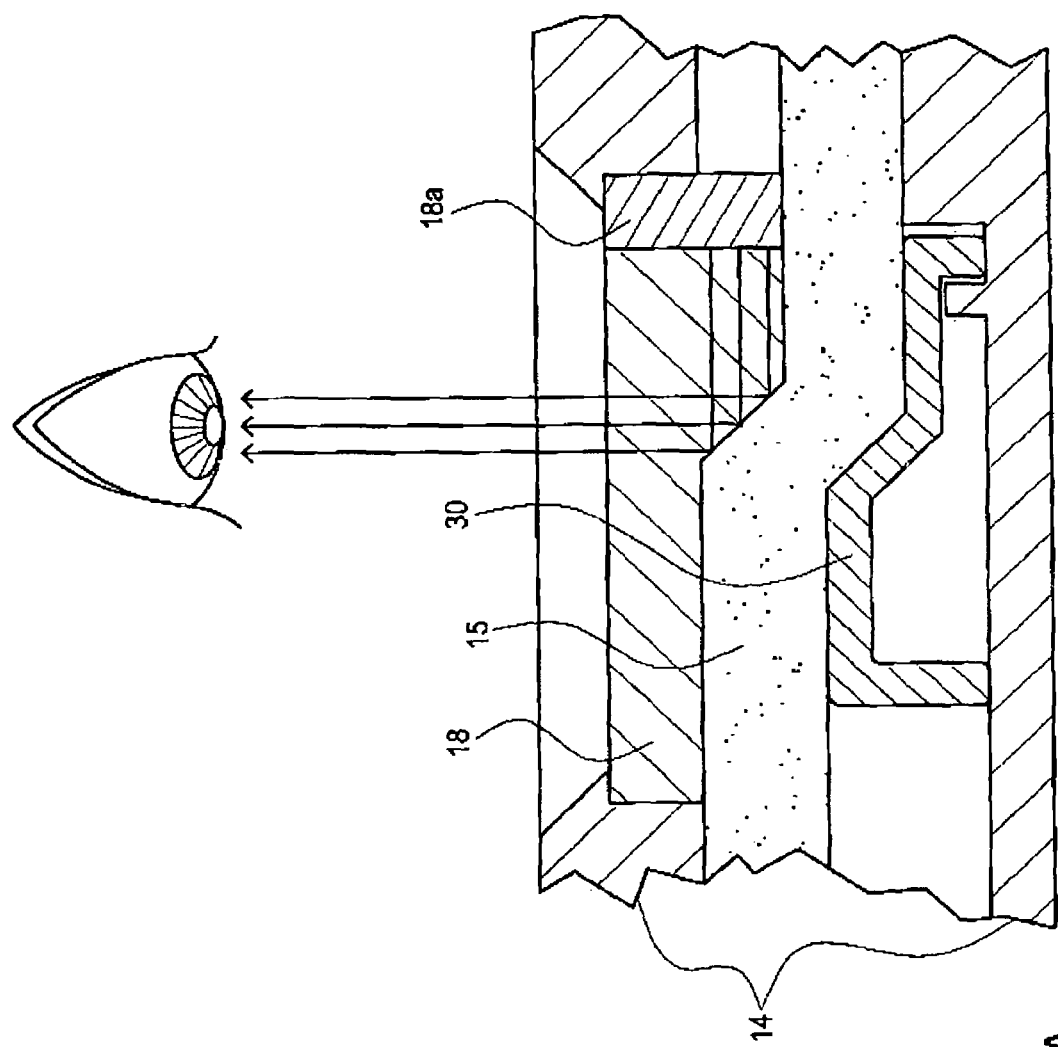
FIG. 3a shows a light pipe indicator window over a saturated absorbent pad including a spring compressor.
Figure 4:
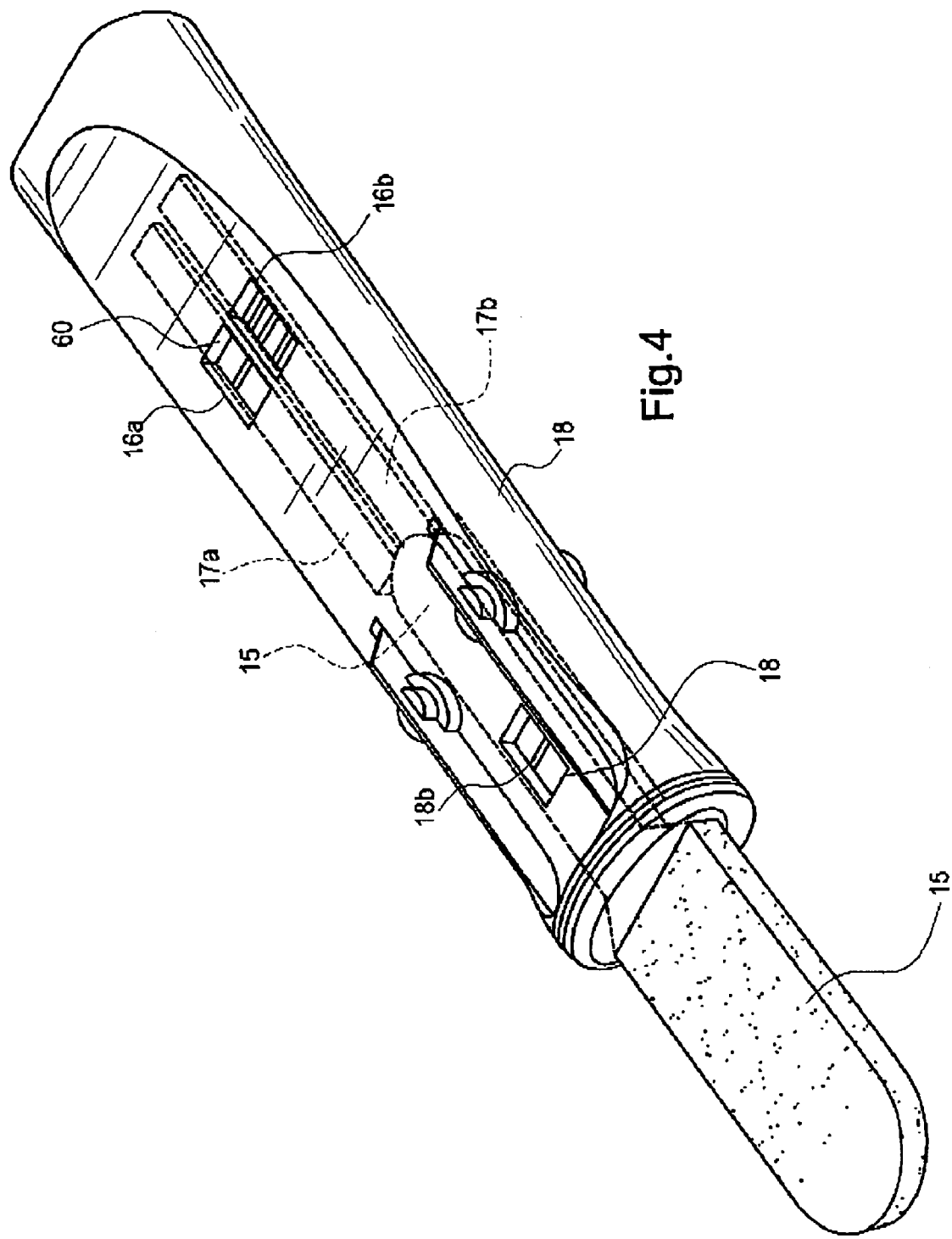
FIG. 4 shows another view of a specimen sample collection device.
Figure 5A:
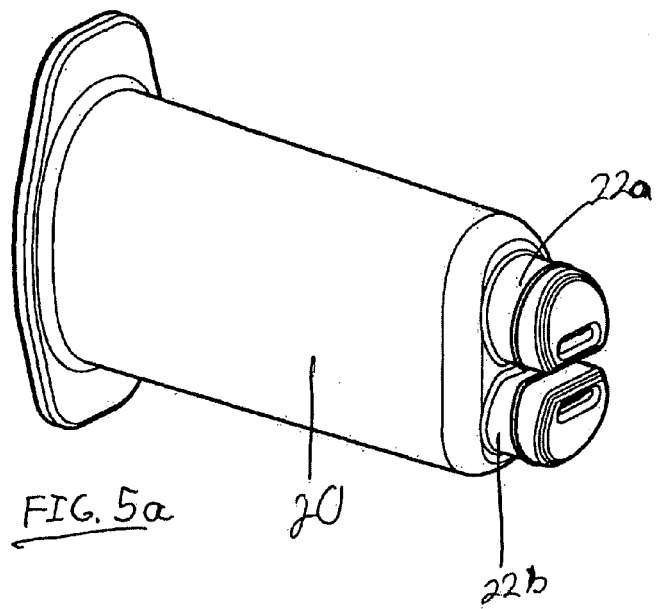
FIGS. 5a, 5b, and 5c show different views of a pad compression tube.
Figure 5B:
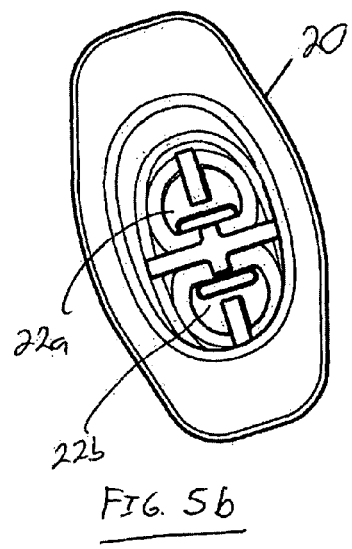
Figure 5C:
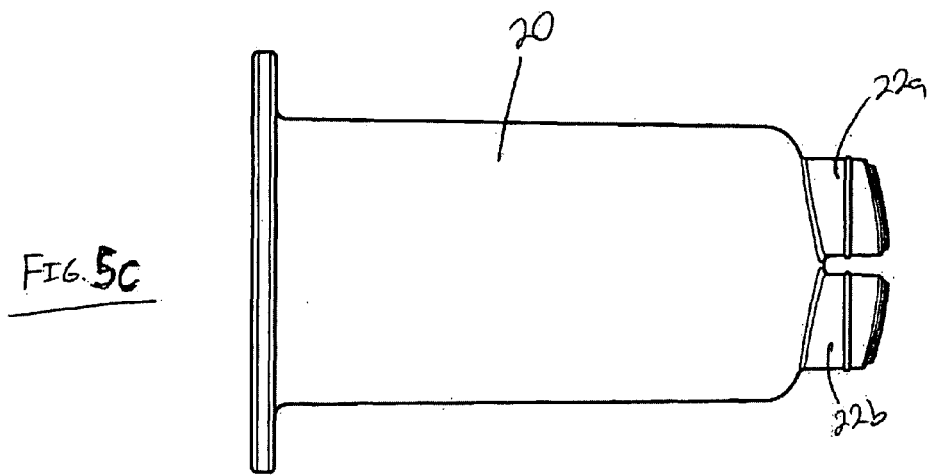

As shown in FIGS. 2-4, sufficiency indicator may be a shaped light pipe 18 with a color or indicator on one end 18a, which is placed in contact with the absorbent pad 15. It is preferably made of styrolux. As show in FIG. 3, when the absorbent pad 15 is saturated with saliva, the refractive properties of the boundary layer between light pipe 18 and absorbent pad 15 change causing more light to pass through the boundary rather than refracting upward. This is visualized by the user as altering the visibility of the indicator, which is seen as a line 18b. As shown in FIG. 3a, a sufficiency indicator with a light pipe may include a spring compressor 30. Spring compressor 30 is shaped to conform to the profile of light pipe 18, thereby assuring continuous contact between absorbent pad 15 and light pipe 18 along their boundary to ensure saturation of absorbent pad 15 alters the refractive properties of the boundary. Using a spring compressor also permits easier manufacture of handle 14, which does not have to be shaped to conform to the contours of light pipe 18.

Alternatively, the sufficiency indicator can be a molded or otherwise manufactured window, convex side downward, and frosted or textured such that when absorbent pad expands by absorption of sufficient sample, the wet absorbent pad touches the inside of the indicator resulting in a change in window clarity, clear spot or symbol indicating that adequate sample volume has been achieved. In this embodiment, an expandable material in contact with an absorbent pad, expands behind and obscures an indicator providing a visual indication that sample volume is adequate when an adequate sample content is reached.

Alternatively, the sufficiency indicator can be a clear window with a small absorbent pad with a colored dot on the inward side, attached on the inside of the window. When the absorbent pad expands against the absorbent paper, the liquid from that pad is transferred to the absorbent paper. Becoming wet, the absorbent pad becomes translucent during which time the colored dot becomes visible through the absorbent paper and becomes visible in the sample adequacy indicator.

Alternatively, the sufficiency indicator can be coated on the inside with a chemically neutral hydrochromic material such that when absorbent pad swells with sample it absorbs, the swollen pad touches the inside of the indicator, reacting with the coating and causing a color change or graphic symbol to appear. Those skilled in the art know that many different chemically neutral hydrochromic coating materials can be used which would not alter the test samples.

Alternatively, the sufficiency indicator is a simple Liquid Crystal Display (LCD) device with two bi polar metal leads pressing into the absorbent pad. When the pad is of adequate saturation, galvanic action causes a small electrical current to flow between the metal leads causing the LCD to darken.

Figure 13:
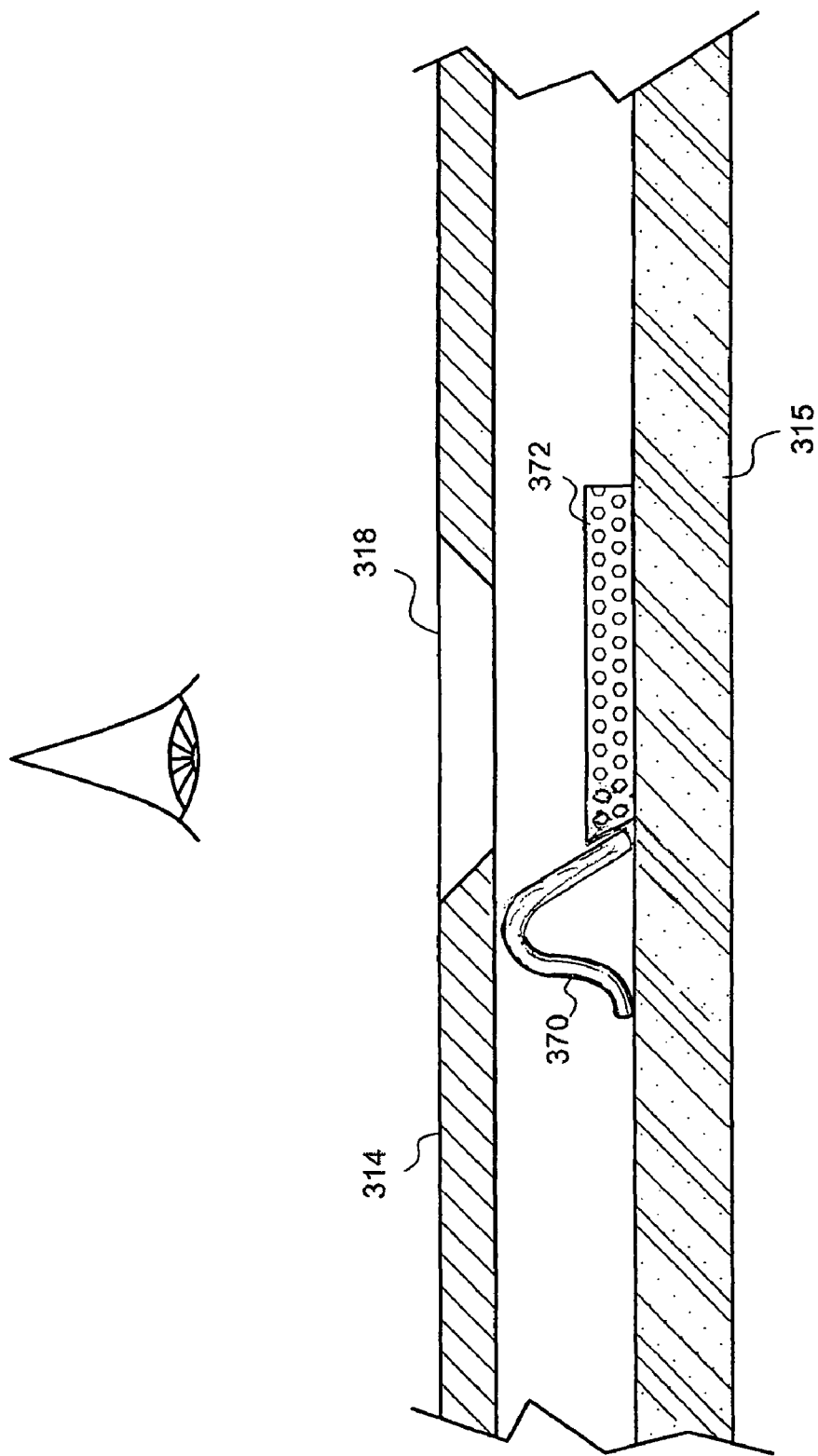
FIG. 13 shows an embodiment of a sample adequacy indicator using a spring set into a sponge.

Alternatively, the sufficiency indicator may be configured as a snap indicator that includes a plastic spring 370 set in a sponge 372 as shown in FIG. 13. Spring 370 is a strip of plastic (or other semi-rigid material such as thin metal) acting as a leaf spring when bent. In an embodiment, a spring 370 is anchored at one end 374 and bent so the non-anchored end 376 is retained by sponge 372 which loses rigidity when wetted. Spring 370 may have an indicator (a color marking or symbol for easy visibility) applied to non-anchored end 376. Sponge 372 is mounted in contact with absorbent pad 315, and sample adequacy indicator window 318 is located above the non-anchored end 376 of spring 370, embedded in handle 314. When absorbent pad 315 absorbs sufficient saliva, as determined by the manufacturer based on the tests to be conducted and the need for retaining verification samples, some of that liquid is transferred to sponge 370 causing it to lose rigidity. When sponge 370 is saturated with saliva the non-anchored end 376 of spring 370 releases and snaps against the inside of sample adequacy indicator window 318 providing an audible indication that sufficient sample volume has been reached, and spring 370 remains in that position to provide visual confirmation as well. If non-anchored end 376 is marked this marking will be visible through sample adequacy indicator window 318 to aid the observer.

Sponge 372 can be cellulose, open cell foam or a similar material that when moistened loses structural rigidity and softens. Sponge 372 may also be a material which dissociates or dissolves when wetted, such as unfired ceramic, clay, salt crystals or sugar crystals. Therefore, in this embodiment the term "sponge" refers to either an actual sponge, or to any material which loses its structural rigidity when wetted.

Figure 7:
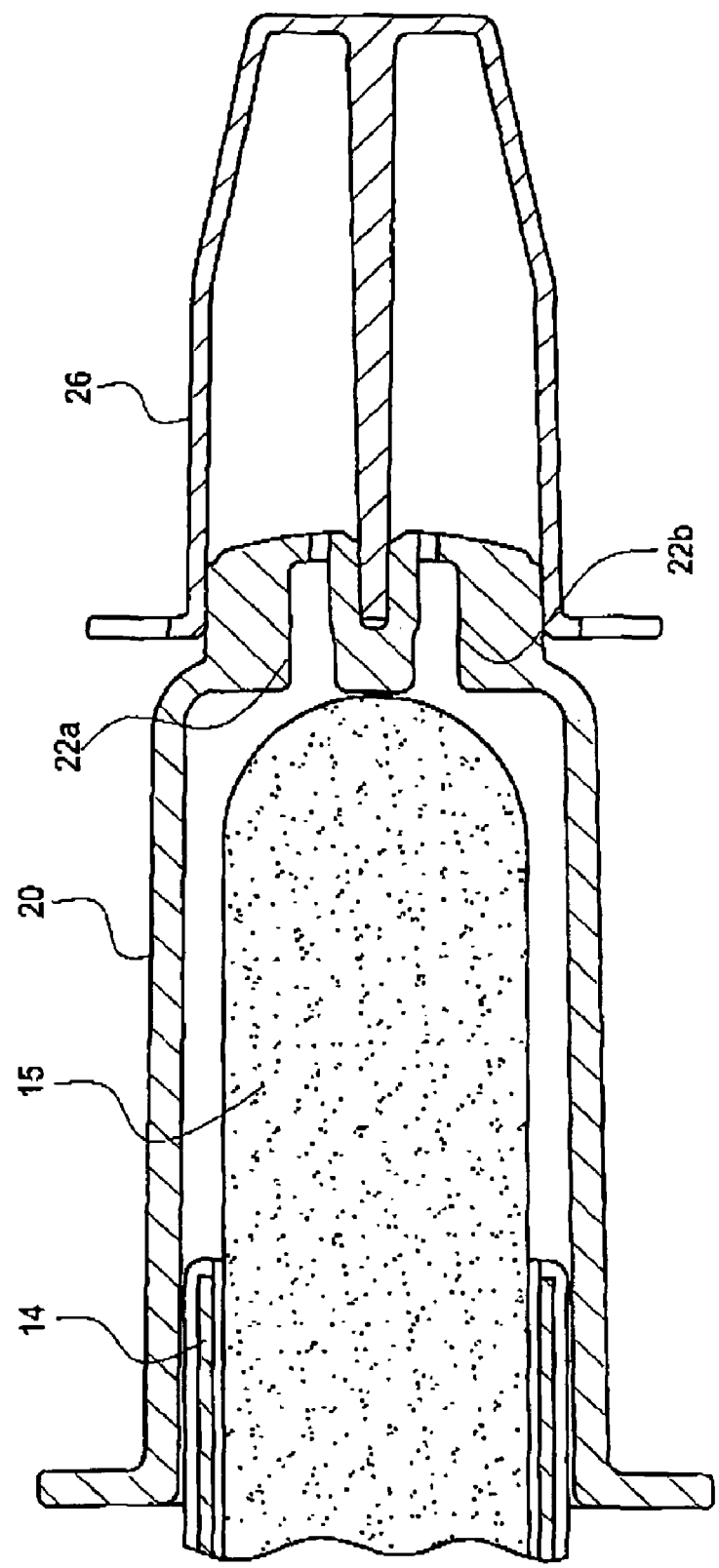
FIG. 7 shows a schematic view of a specimen sample collection device and test system with a pad compression tube attached to a handle.

Fluids are removed from absorbent pads by squeezing sample from the pad material through compression tubes. Alternate methods of fluid removal may be envisaged as necessary to facilitate removal of said liquid from the pad. Such techniques include vortexing, squeezing, centrifugation and treatment with an agent to promote removal of non-constituent components of the pad material among others. Pushing the handle into the pad compression tube compresses the absorbent pad expelling specimen from absorbent pad into the pad compression tube. As shown in FIG. 7, pad compression tube 20 when inserted over absorbent pad 15 and one end of handle 14 is in fluid communication with absorbent pad 15.

Pad compression tube 20 can have one or more channels and one or more outlets. FIG. 8 shows a dual outlet dual channel pad compression tube 120 having two outlets 122a, 122b. FIG. 9 shows a single outlet single channel pad compression tube 150 with a single outlet 152. FIGS. 1, 5a, 5b, 5c, and 7 show a dual outlet single channel pad compression tube 20 with two outlets 22a, 22b.

As seen in FIG. 7, pad compression tube 20 fits over and around the absorbent pad 15, which is partially contained within the handle 14 (see also FIG. 10), and tube 20 goes over the end of the handle 14. As shown in the embodiment in FIG. 8, handle 114 can be provided with a ridged lock 160 which fits in a depressed key 162 on a pad compression tube 120. Absorbent pad 115 is pushed into pad compression tube until "locked" into place for safety preventing contamination and infectious transfer.

Pad compression tubes are is made of polypropylene or acrylic or other suitable material. Pad compression tubes can be provided with a tube cap, see 24 in FIG. 1 made of polypropylene or other suitable material.

A dual outlet dual channel pad compression tube 120 fits around a split absorbent pad 115. Pushing the handle 114 into the dual outlet dual channel pad compression tube 120 compresses the split absorbent pad 115, expelling specimen from split absorbent pad 115 into the dual outlet dual channel pad compression tube 120. Dual outlet dual channel pad compression tube 120 when inserted over split absorbent pad 115 and on end of handle 114 is in fluid communication with split absorbent pad 115. As shown in FIG. 8, the dual outlet dual channel pad compression tube 120 includes a structural barrier 140 that separates the two parts of the split absorbent pad 115, such that when the pad 115 is compressed upon entry into the compression tube 120, the saliva sample from each said part of the pad 115 remains distinct and separate. Next, each separated saliva sample flows or is compressed into its own Eppendorf-style collection tube 126, which is attached to a compression tube, see 120 in FIG. 8 and 150 in FIG. 9.

As shown in FIG. 14, in another embodiment a specimen sample collection device and test system 412 may include a large absorbent pad 415*a* and a small absorbent pad 415*b* in parallel with one another within handle 414. In this case "large" and "small" refer to the volume of liquid sample absorbed and not necessarily to the physical dimensions. Large absorbent pad 415*a* is in fluid contact with sample adequacy indicator 418, but not in fluid communication with lateral flow test strip 416. The size of large absorbent pad 415*a* is determined by the desired size of sample to be retained for verification or separate analyses. Small absorbent pad 415*b* is in parallel with large absorbent pad 415*a* and in fluid contact with test one or lateral flow test strips 416, but not in fluid contact with sample adequacy indicator 418. In FIG. 14 large absorbent pad 415*a* and small absorbent pad 415*b* are positioned in parallel with one above the other, but not in fluid contact with one another. The absorbent pads may be separated by a small gap or by an impermeable membrane 480. Alternatively, large absorbent pad 415*a* and small absorbent pad 415*b* may be aligned side-by-side. Rapid results may be viewed through viewing window 460.

In use, both large absorbent pad 415*a* and small absorbent pad 415*b* are placed in a patient's mouth simultaneously, preferably under the tongue, until the sample adequacy indicator 418 is triggered indicating sufficient volume of saliva has been collected. Immediate test results may be observed through the test strip viewing window 460. Parallel absorbent pads with separate test strips and adequacy indicator reduce the time required to obtain both immediate test results and adequate volume for retained liquid specimens. Each pad's dimensions can be optimized for its function. Large and small absorbent pads 415*a* & *b* may be of differing absorption characteristics which are optimized for the particular testing regime. Large absorbent pad 415*a* may be optimized for maximum absorption volume while small absorbent pad 415*b* may be optimized for transferring maximum volume of liquid sample to test strip 416. The length of the test strips and the overall length of the specimen sample collector 412 can be reduced as well.

The pad compression tube outlets can also each contain a particulate filter (not shown). Each distinct and separate saliva sample passes through its own particulate filter remaining distinct and separate.

The pad compression tube can contain a buffer solution to stabilize the sample obtained for analysis or testing. Suitable buffers include an aqueous solution with any of a variety of salts including sodium chloride, sodium phosphate, ethylene diamine tetra acetic acid (EDTA) salts or others. Buffer solution may contain a preservative to maintain the integrity of the sample and minimize degradation. This preservative serves to inhibit proteolytic properties of enzyme materials that can cause destruction of the antibody molecules being tested with the device over time. The types of compounds that can be considered as conferring preservative properties include enzyme inhibitors, anti-bacterial agents, bacteriostatic molecules, and anti-fungal compounds among others. Within the sub-group of bacteriostatic molecules, there are a number which can be added to also inhibit the growth of microorganisms. Such compounds include ProClin® (in various formulations) sodium azide and thimerosal.

The buffer solution may also include a detergent material, which improves antibody removal from the absorbent pad material, when desired. Preferred examples of this are Tween-20 (chemical name polyoxyethylene sorbitan monooleate) and sodium dodecyl sulfate (SDS), although other examples, e.g. Triton X-100, chlorhexidine and others may also be used. Tween-20 for example, is also useful for prevention of non-specific binding of required antibody molecules to unwanted solid surfaces. Typical concentrations of Tween-20, for instance, necessary to achieve the desired effect, range from 0.1%-1%. Similarly, low molecular weight alcohols (ethanol, methanol, butanol, etc.) in low concentrations (0.1-4.0%) can be introduced as additional analyte-releasing agents, depending upon the material under investigation.

Those skilled in the art will know that there are many possible agents capable of being used as "buffering components". Alternately the pad collection tube may contain no reagent or liquid whatsoever. Alternately, the pad collection tube may contain a non-fluid containing buffer, i.e. a buffer without liquid, commonly referred to as a "dry buffer". The permutation and concentrations of any agents used as part of the collection procedure will be optimized for the collection of specific target molecules. In the case of analytes or materials that are difficult to release from the pad material under "normal" buffer conditions, for example "sticky" materials such as the drug THC, or steroid hormones (including testosterone, estradiol, progesterone and others), various reagents including small quantities (less than 5%) of an alcohol, e.g. methanol, ethanol, propanol, iso-propanol may be added to facilitate analyte release.

Typical buffers include phosphate buffered saline consisting of, for example: 10 mmol/L Sodium Phosphate Dibasic; 150 mmol/L Sodium Chloride; 5 mmol/L Disodium Ethylenediamine Tetraacetate (EDTA); 31 mmol/L Sodium Azide; Adjusted to neutral pH of 7.2.

Collection tubes can be a chambered collection tube 26, as shown in FIGS. 1, 6*a*, 6*b*, and 6*c*, or individual collection tubes 126, as shown in FIGS. 8 and 9.

Figure 6A:
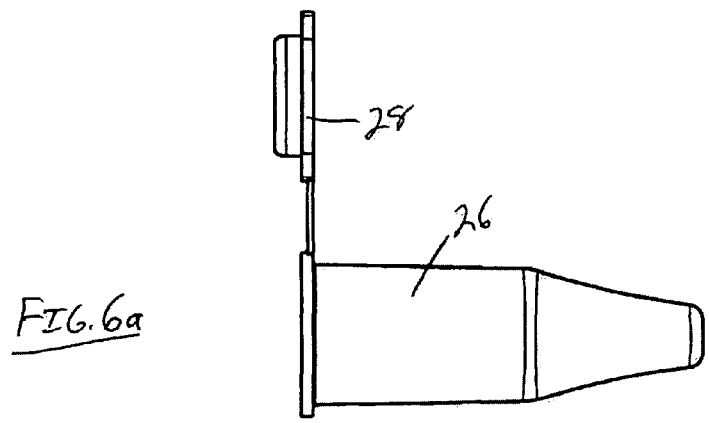
FIGS. 6a, 6b, and 6c show different views of a chambered collection tube.
Figure 6B:
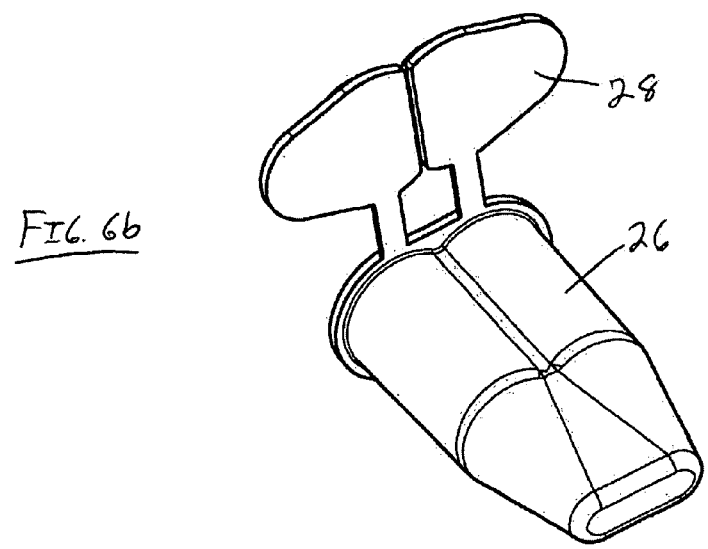
Figure 6C:
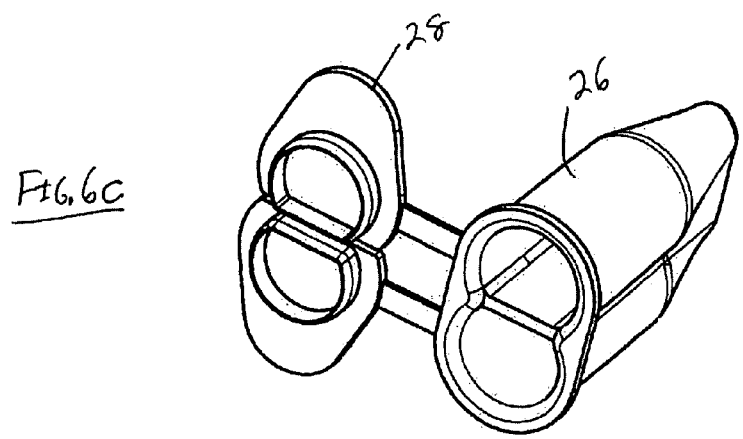

Chambered collection tube 26 is shown in different views in FIGS. 6*a*, 6*b*, 6*c*. Collection tubes fit over the end of the pad compression tube and have one or more chambers for receiving and holding collected samples. These chambers or compartments are separated allowing samples to remain distinct and free from contamination. In an embodiment, collection tube, at 26 in FIG. 1 and at 126 in FIGS. 8 and 9, when inserted on end of pad compression tube, 20 in FIG. 1, 120 in FIG. 8, and 150 in FIG. 9 is in fluid communication with pad compression tube. Collection tube, at 26 in FIG. 1 and at 126 in FIGS. 8 and 9, can be provided with a tube cap, at 28 in FIG. 1, and at 128 in FIGS. 8 and 9, sealing the tubes.

Eppendorf-type collection tubes 126, in FIGS. 8 and 9, collect the separate and distinct saliva samples once they pass through a pad compression tube. Eppendorf-type collection tubes 126 are conical at their closed end, round at the open end, and comprised of flexible lids 128 that remain attached to the tube 126 whether open or closed. The Eppendorf-type collection tubes 126 may be attached together on the outside surface. The Eppendorf-type collection tubes 126 remain inwardly distinct in that each receives one of the distinct and separate saliva samples and said samples remain separate and distinct once in the Eppendorf-type collection tubes 126. The Eppendorf-type collection tube lid 128 is then closed, retaining the fluid sample's integrity and quantity.

Handles, pad compression tubes, and collection tube can be made using any number of different processes familiar to those with skill in the art, such as by injection molding, compression molding, casting; incorporating materials such as thermoplastics, thermosets, glass, metal, etc. The light pipe indicator window can be made of clear material, e.g. glass, plastic, or Perspex.

In a preferred embodiment, handle 14 is assembled from two elongated pieces of General Purpose Styrene 14a & b which snap together over a portion of the absorbent pad. See FIG. 10. The two halves of handle 14 are then sealed together using ultrasonic welding methods. Those of skill in the art know that the handle can be made of any one of numerous materials.

In a preferred embodiment the apparatus is intended for collecting saliva, though other embodiments for collecting samples other than saliva exist (such as collection of water for environmental testing purposes, urine analysis for drug testing, bioavailability testing in the pharmaceutical industry and many others), absorbent pad is placed in the mouth under the tongue. Absorbent pad expands when a specimen sample is received. When indicator indicates sufficient sample has been obtained, Indicator provides a visual indication of the same.

In order to enrich the specimen with immunoglobulins, which are present under the lip line at the end of the collection process, the specimen sample collection device is taken and "swabbed" once across the gums from one side to the other, then reversed and swabbed across the gum line a second time in the opposite direction.

In order to collect saliva, the specimen sample collection device is placed under the tongue and allowed to remain there until the visual indicator in the device—a light pipe showing a blue coloration—disappears completely. The typical collection time for sample adequacy is in the range of 1-2 minutes. The sample adequacy indicator may be observed by a second person or in the event of the sample being collected in the privacy of the home, by a donor in isolation The device may be removed from the mouth to visually inspect for adequate sample volume and replaced under the tongue immediately without detriment to the collection or subsequent test procedure.

In operation using a split absorbent pad 115 and a dual outlet dual channel pad compression tube 120, the user places the pad 115 into the dual outlet pad compression tube 115 with the split end facing downwards, and places the Eppendorf-type collection tube 126 on the outlets 122 of the dual outlet pad compression tube 120, and pushes on handle 114, forcing the pad 115 all the way down to the bottom of the compression tube 120 until the end of the handle 114 can be pushed no closer to the bottom of the compression tube 120. Pushing expels specimen from split absorbent pad 115, which then travels in fluid communication through the dual outlet pad compression tube 120, through the outlets 122 and into collection tubes 126. The collection tubes 126 thus provide samples for supplemental or confirmatory testing as well as for independent storage or transportation. Two samples are thus provided. Depending upon the dimensions and type of pad material used the individual forks of the absorbent material will release between 0.3 ml and 2 ml of pure saliva. In instances where the individual samples, are to be transported to a laboratory or remote location, or are not for immediate testing, a preservative buffer may be introduced either in the compression tube or the collection receptacles to maintain the integrity of the sample so collected. The buffer may be a liquid or dry buffer. In instances where the samples are to be tested immediately, or at the point-of-care, the device may be supplied without buffer. In order to determine the volume of specimen received by this action, graduated tubes, such as small Eppendorf tubes, available "off the shelf" from a number of vendors, may be used. Alternatively, where no duplicate sampling is required, the collection tube can be a single channel collection receptacle or Eppendorf tube. Depending upon sampling requirements alternative customized collection tubes may be adapted for use with the invention. Each of the tubes used in connection with the collection tool are fitted with individual caps for sealing purposes. These caps may be tamper-proof for evidentiary purposes. Similarly, the pad compression tube can be provided with a cap or caps for sealing.

Figure 10:
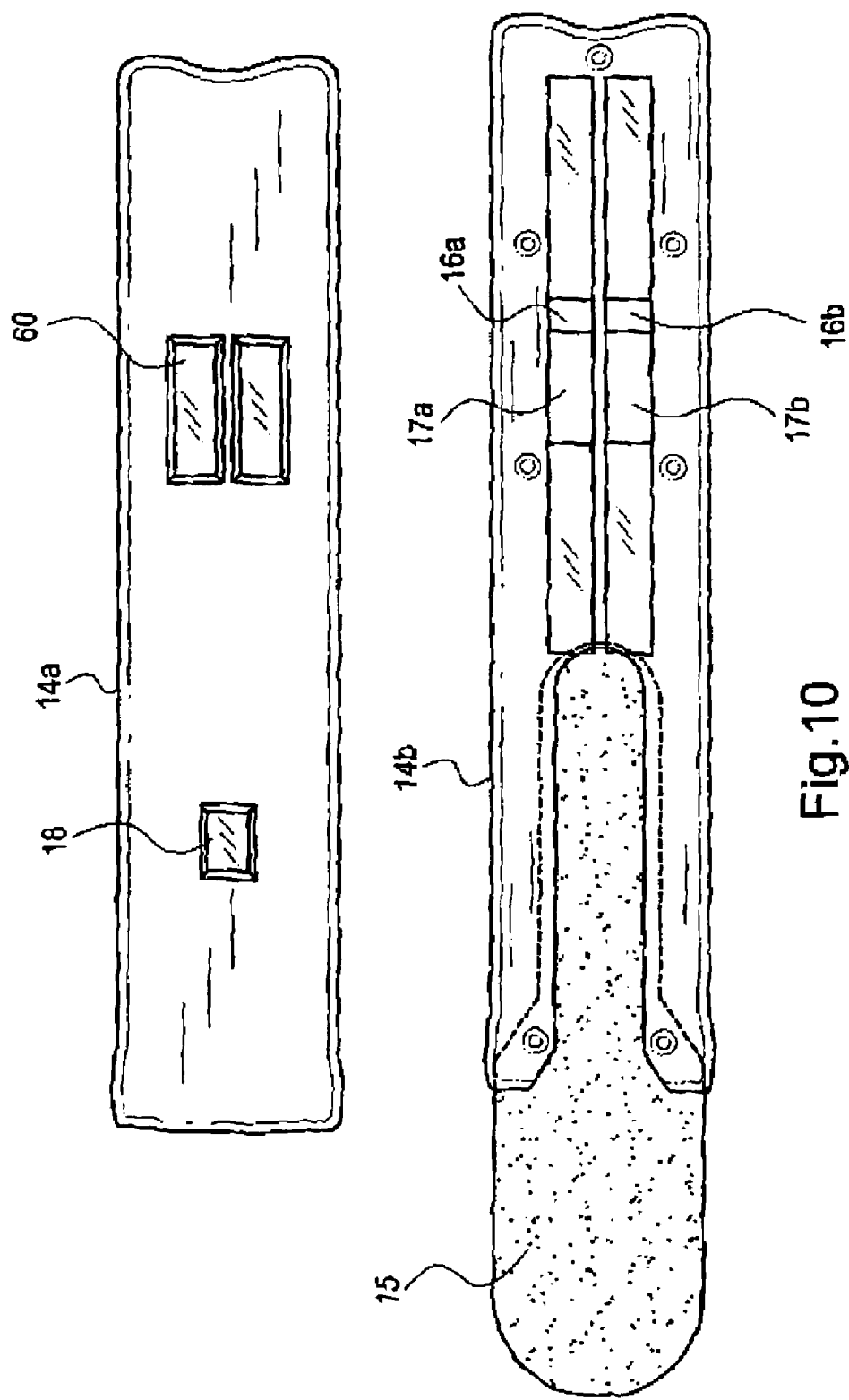
FIG. 10. shows the interior layout of a specimen sample collection device.

As shown in FIG. 10, the specimen sample collection device 10 can be provided with one or more lateral flow test strips 16a, 16b in the handle 14 in fluid communication with the absorbent pad 15 by one or more membranes 17a, 17b. Such tests strips, for example ICT strips are commonly used in the diagnostic industry today, to screen for a plethora of diseases including HIV, streptococcus A & B, hepatitis A, B & C, cardiac markers (e.g. troponin 1, troponin T, myoglobin), tumor markers (e.g. prostate specific antigen (PSA), alpha-fetoprotein (AFP), etc.), glucose, cholesterol and others.

The test strip is coated or "striped" with one or more analyte of interest, together with a control material usually Protein A-gold coated to human IgG to verify that the test strip is working appropriately. Such strips are now very commonly available and well characterized. After a short period of time (which may vary from 2 to 20 minutes), a Control Line will appear on the test strip, and in instances of a positive specimen a second line (the Test Line) will appear indicating positivity for the analyte of interest.

The test strip is comprised of reagents that test qualitatively (for the presence or absence of analytes or substances) and/or semi-quantitatively (providing an estimate of the quantity) of the chemical(s)/substances for which the device tests within the fluid sample. In the preferred embodiment the test strip is located in the collector handle housing, above the attachment loci of the absorbent pad. The collector handle housing has a window-type opening above a portion of the test strip through which results from the test strip can be viewed.

A reagent test strip comprised of at least one reagent chemical that upon contact with the chemical for which it tests or a by-product of the chemical for which it tests in the testing fluid, undergoes a chemical reaction which produces or activates an indicator, preferably visual, of the presence or absence and/or quantity of the chemical for which it tests.

The test system may be applied to a number of different diseases, and analytical tests, which includes HIV, drugs of abuse, bacteria, viruses, environmental toxins and others. Reaction times and run times will vary depending upon the characteristics of individual test strips, which are optimized to achieved maximum sensitivity and specificity. The characteristics of each individual test will be defined in the respective package insert for the products, however, as an example, an HIV test optimized for oral fluid detection using the specimen sample collection device will provide results within a period of 10-20 minutes with a sensitivity greater than 95% and a specificity of greater than 99%. What should be understood in the case of an HIV test is that the appearance of a Test Line in the presence of a Control Line is indicative of an initially positive or non-negative result.

When more than one test strip is provided they are arranged side-by-side on the handle 14, as shown in FIGS. 4 and 10, at 16a, 16b. In this embodiment, saliva collected in identical fashion to the embodiments described above, is transferred to two test strips instead of one by two membranes, 17a, 17b. Using this configuration, a multiplicity of analytes, for instance drugs of abuse, including but not limited to the NIDA-5 series of drugs, benzodiazepines, Oxycodone, and others, as well as therapeutic drugs and multiple infectious diseases for instance may be detected simultaneously using a single oral fluid collection device and test system. Test strips for the NIDA-5 series of drugs have been optimized in the specimen sample collection device to run within 15 minutes from the time sample adequacy has been achieved.

In this embodiment, the reagent test strips 16 are located in the collector handle 14 housing with a window-type opening 60 above each test strip 16, or, alternatively, a single window-type opening above all the test strips. Each test strip contains a reagent test for analyzing the qualitative (presence or absence) and/or quantitative data of the chemical for which it tests within the fluid sample. One of skill in the art would understand that each test strip may test for a different chemical or the same chemical as any other test strip. In the preferred embodiment, the test strips extend linearly down the length of the collector handle housing, parallel to one another. In another embodiment, the test strips may be adjacent to one, two or more additional test strips.

In embodiments including a test strip 16 under a test strip opening 60, the results may be read visually or may be read by electronic reading devices including pocket-PC devices, PDAs and others. In the preferred embodiment of this invention a pocket-PC driven system, utilizes proprietary software to digitally record images from the lateral flow test strips. The reader combines a "Pocket PC" (PDA-sized) reading system, printing device, camera and software, capable of reading multiple lines within a pre-set reading window. Once the specimen sample collection device incorporating one or more test strips has run and the immunochromatographic test results have been observed visually, (after the pre-established reaction time is over), a plastic cap is placed over the absorbent collection pad of the specimen sample collection device, if desired, then the opposite end of the device (handle-first) is inserted into the port of the hand-held reading device. The reading device initially does a diagnostic "self test" to ensure that the reader is working appropriately then performs a read out of the intensity of the coloration of the individual line (or lines) on the test strip (or strips). The results of this are fed automatically to a printing device, which prints out a permanent record of the results for each drug or other analyte being tested. The visual appearance of a line, or the confirmation of a line in the case of drug tests using the hand-held reading system is an indication that the test is negative or non-positive for that particular analyte or drug. This is the opposite of what one would find for similar tests for HIV and other analytes where the presence of a Test Line in the presence of a Control Line is indicative of a positive or non-negative result. The invention provides visually read, qualitative results, which may be quantitated using available electronic, digital or other format readers. These in turn may be either small, PDA-sized (hand-held) systems or portable and non portable instruments that utilize electromagnetic radiation, chemiluminescence, digital photography and other techniques, while providing a digital printout of the quantitative results obtained.

Fluid forced through separate porous filters in pad compression tube and into mutually distinct gradiated Eppendorf-type tubes attached to the pad compression tube outlets. Each Eppendorf tube is then bar coded. A bar code may further be provided on the specimen sample collection device handle. A recess is molded into the specimen sample collection device handle and the bar code is imprinted thereon.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

We claim:

1. A specimen sample collection device and test system, comprising:
    a handle having opposing first and second ends, including a sufficiency indicator, and first and second uni-directional locking teeth disposed on opposing sides of said handle;
    an absorbent pad partially contained within said handle and extending out from said handle first end;
    a pad compression tube insertable over said absorbent pad and around said first end of said handle, said pad compression tube including one or more outlets and a plurality of locking holes on opposing sides of said pad compression tube for lockingly engaging said locking teeth, said locking holes spaced apart lengthwise on said compression tube to lock said pad compression tube over said handle first end in progressively tighter compression positions; and,
    a collection tube sealingly connectable to a pad compression tube outlet, said collection tube including one or more sample chambers, wherein when said collection tube is sealingly connected to a pad compression tube outlet at least one of said corresponding one or more sample chambers is in fluid communication with said pad compression tube and said absorbent pad.

2. The apparatus of claim 1, wherein said indicator is a light pipe, said light pipe including a first end surface with a marking and a second surface in physical contact with said absorbent pad creating a refractive boundary, said second surface oriented at an angle of incidence to said first surface such that when the absorbent pad absorbs a sufficient liquid sample the refractive properties of said boundary alter the observability of the mark; and,
    wherein said apparatus includes a spring compressor within said handle, said spring compressor shaped to conform to the profile of said second surface of said light pipe such that the compression spring forces said absorbent pad into contact with said second surface of said light pipe.

3. The apparatus of claim 1, wherein said indicator comprises a window, a sponge and a loaded spring set into said sponge, wherein said sponge is in fluid communication with the absorbent pad, such that when the sponge is softened by absorption of liquid the spring partially or completely disengages from the sponge and snaps into view of said window, providing visual and audible indication that sample volume is adequate.

4. The apparatus of claim 1, wherein said indicator comprises a clear window and a material which expands when wetted, said material in fluid communication with said absorbent pad, wherein the expandable material will expand to obscure the window when sample volume is adequate.

5. The apparatus of claim 1, wherein said indicator comprises an electrical circuit, said electrical circuit comprising:
   a pair of leads composed of galvanically dissimilar conductors connected across said absorbent pad, at a location along the absorbent pad selected to indicate sufficient liquid sample has been absorbed, and
   a liquid crystal display connected in series between said pair of leads;
   such that, when liquid saturates the absorbent pad up to said location, a galvanic couple is created between said pair of leads, allowing electric current to flow through said liquid crystal display and change the liquid crystal display state, thereby providing visual indication of sample adequacy.

6. The apparatus of claim 1, wherein said indicator comprises a window and a paper with a colored dot located on the inward surface of said paper, wherein said paper becomes translucent when saturated with liquid, and further wherein said paper is located in close proximity to said absorbent pad at a location along the length of said absorbent pad, such that when the absorbent pad becomes saturated with liquid at least to said location the absorbent pad expands to contact the paper, thereby transferring liquid to the paper allowing the paper to become saturated and thereby making the dot visible through said window.

7. The apparatus of claim 1, wherein the indicator is a window coated on the inside with a hydrochromic material such that when absorbent pad swells with sample it absorbs, the wet, swollen pad touches the inside of the window, reacting with the coating and causing a color change or graphic symbol to appear.

8. The apparatus of claim 1, wherein said absorbent pad is rounded in that portion protruding from said handle.

9. The apparatus of claim 1, wherein said absorbent pad is split, divided into two parts and connected at a base of said absorbent pad.

10. The apparatus of claim 9, wherein said pad compression tube defines two chambers into which a corresponding part of said split absorbent pad can be inserted and each of said pad compression tube chambers has includes an outlet.

11. The apparatus of claim 1, wherein said handle is further provided with a bar code number uniquely identifying said handle.

12. The apparatus of claim 1, further comprising:
   said handle further includes a test strip viewing window disposed therein;
   an analyte test strip contained within said handle in view of said viewing window; and
   a membrane contained within said handle, wherein said said absorbent pad is in fluid communication with said test strip through said membrane.

13. The apparatus of claim 12, further comprising two or more analyte test strips contained within said handle in view of said viewing window and two or more corresponding membranes contained within said handle, wherein said absorbent pad is in fluid communication with each of said test strips through said corresponding membranes.

14. The apparatus of claim 12, further comprising two or more analyte test strips contained within said handle in view of said viewing window and a single membrane contained within said handle, wherein said absorbent pad is in fluid communication with each of said test strips through said membrane.

15. The apparatus of claim 1, wherein the absorbent pad is folded over upon itself.

16. A specimen sample collection device and test system, comprising:
   a handle having opposing first and second ends, said handle further including a sufficiency indicator, a viewing window for viewing results from a test strip, wherein said sufficiency indicator and test strip are located along opposing sides of said handle;
   an analyte test strip contained within said handle;
   a first absorbent pad partially contained within said handle and extending out from said first end, said first absorbent pad in fluid communication with said sufficiency indicator but not in fluid communication with said test strip, wherein said first absorbent pad is sized to collect a predetermined volume of liquid specimen;
   a second absorbent pad partially contained within said handle and extending out from said first end, wherein said second absorbent pad is in fluid communication with said test strip but not in fluid communication with said sufficiency indicator and wherein said second absorbent pad is parallel to said first absorbent pad;
   a pad compression tube insertable over said first and second absorbent pads and around said first end of said handle, said pad compression tube including one or more outlets; and,
   a collection tube having one or more sample chambers, wherein each of said one or more collection tube chambers is sealingly connectable to one of said one or more pad compression tube outlets in fluid communication with said pad compression tube and said first and second absorbent pads.

17. The apparatus of claim 16 further comprising an impermeable membrane separating said first and second absorbent pads.

18. The apparatus of claim 16 or 17, wherein said handle includes a pair of uni-directional locking teeth on opposing sides of said handle and wherein said pad compression tube includes a plurality of locking holes on opposing sides of said pad compression tube for lockingly engaging said locking teeth, said locking holes spaced apart lengthwise on said compression tube to lock said pad compression tube over said handle in progressively tighter compression positions.

* * * * *